United States Patent
Lee et al.

(10) Patent No.: US 9,841,403 B2
(45) Date of Patent: Dec. 12, 2017

(54) DIFFERENTIATING ANALYTES DETECTED USING FAST SCAN CYCLIC VOLTAMMETRY

(75) Inventors: Kendall H. Lee, Rochester, MN (US); Dong-Pyo Jang, Sungnam (KR); Inyong Kim, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 526 days.

(21) Appl. No.: 13/555,965

(22) Filed: Jul. 23, 2012

(65) Prior Publication Data

US 2013/0023745 A1    Jan. 24, 2013

Related U.S. Application Data

(60) Provisional application No. 61/510,366, filed on Jul. 21, 2011.

(51) Int. Cl.
| | |
|---|---|
| *A61B 5/05* | (2006.01) |
| *G01N 27/48* | (2006.01) |
| *A61B 5/00* | (2006.01) |
| *A61B 5/1473* | (2006.01) |

(52) U.S. Cl.
CPC .......... *G01N 27/48* (2013.01); *A61B 5/1473* (2013.01); *A61B 5/6868* (2013.01)

(58) Field of Classification Search
CPC ...... G01N 27/48; A61B 5/1473; A61B 5/6868
USPC ........................................ 600/345, 347, 365
See application file for complete search history.

(56) References Cited

U.S. PATENT DOCUMENTS

| | | | |
|---|---|---|---|
| 5,650,061 | A | 7/1997 | Kuhr et al. |
| 5,806,517 | A | 9/1998 | Gerhardt et al. |
| 6,164,284 | A | 12/2000 | Schulman |
| 7,209,788 | B2 | 4/2007 | Nicolelis |
| 7,440,806 | B1 | 10/2008 | Whitehurst et al. |
| 7,747,318 | B2 | 6/2010 | John |
| 7,899,545 | B2 | 3/2011 | John |
| 7,901,368 | B2 | 3/2011 | Flaherty et al. |
| 8,140,152 | B2 | 3/2012 | John |
| 8,315,703 | B2 | 11/2012 | Lozano |
| 8,359,100 | B2 | 1/2013 | Cameron |
| 8,433,415 | B2 | 4/2013 | Leiter |
| 8,473,060 | B2 | 6/2013 | Leiter |

(Continued)

FOREIGN PATENT DOCUMENTS

| | | | |
|---|---|---|---|
| WO | WO 2010/083208 | 7/2010 | |
| WO | WO 2011/028608 | * 3/2011 | ............... A61N 1/04 |

(Continued)

OTHER PUBLICATIONS

Anastassiou et al. "Subsecond Voltammetric Separation between Dopamine and Serotonin in the Presence of Ascorbate." Analytical Chemistry. Oct. 2006. Volume 78, No. 19. pp. 6990-6998.*

(Continued)

*Primary Examiner* — Tiffany Weston
(74) *Attorney, Agent, or Firm* — Fish & Richardson P.C.

(57) ABSTRACT

This document provides methods and materials involved in differentiating analytes detected using a FSCV method. For example, methods and materials for using paired pulse voltammetry to discriminate analytes based on their adsorption characteristics to an electrode (e.g., a carbon fiber electrode) are provided.

21 Claims, 7 Drawing Sheets

(56) References Cited

U.S. PATENT DOCUMENTS

| | | |
|---|---|---|
| 2002/0013612 A1 | 1/2002 | Whitehurst |
| 2004/0108223 A1 | 6/2004 | Jansson |
| 2006/0009814 A1 | 1/2006 | Schulman |
| 2006/0173509 A1 | 8/2006 | Lee et al. |
| 2006/0195157 A1 | 8/2006 | Lee |
| 2006/0241717 A1 | 10/2006 | Whitehurst |
| 2007/0026440 A1 | 2/2007 | Broderick et al. |
| 2008/0179197 A1 | 7/2008 | Wu |
| 2008/0258116 A1 | 10/2008 | Viticoli et al. |
| 2008/0288023 A1 | 11/2008 | John |
| 2010/0032316 A1 | 2/2010 | Wu |
| 2010/0312305 A1 | 12/2010 | Leiter |
| 2012/0088983 A1 | 4/2012 | Jung et al. |
| 2012/0165634 A1 | 6/2012 | Lee et al. |
| 2015/0360032 A1 | 12/2015 | Bennet |
| 2016/0192872 A1 | 7/2016 | Lee |

FOREIGN PATENT DOCUMENTS

| | | |
|---|---|---|
| WO | WO2014110263 | 7/2014 |
| WO | WO2015021470 A1 | 2/2015 |

OTHER PUBLICATIONS

Jang et al. "Paired pulse voltammetry for differentiating complex analytes." The Royal Society of Chemistry. 2012. 137. pp. 1428-1435.*

Lane, et al. "Differential Double Pulse Voltammetry at Chemically Modified Platinum Electrodes for in vivo Determination of Catecholamines." Analytical Chemistry, vol. 48, No. 9. Aug. 1976. pp. 1287-1293.*

International Search Report and Written Opinion in International Application No. PCT/US2010/046807, mailed May 31, 2011, 9 pages.

International Preliminary Report on Patentability in International Application No. PCT/US2010/046807, mailed Mar. 8, 2012, 6 pages.

Abosch et al., "Stimulation of the subthalamic nucleus in Parkinson's disease does not produce striatal dopamine release," *Neurosurgery*, 2003, 53:1095-1102; discussion 1102-1095.

Adams, "In vivo electrochemical measurements in the CNS," *Prog Neurobiol*, 1990, 35(4):297-311.

Agnesi et al., "Wireless Instantaneous Neurotransmitter Concentration System-based amperometric detection of dopamine, adenosine, and glutamate for intraoperative neurochemical monitoring," *J Neurosurg.*, 2009, 111:701-711.

Aillon et al., "Near real-time measurement of glutamate concentration changes using biosensors in place of traditional methodologies," in Phillips PEM, Sandberg SG, Ahn S, Phillips AG (ed): proceeding of the 12th international conference on in vivo methods 2008. University of British Columbia, Vancouver, Canada. 2008, pp. 108-110.

Albin et al., "The functional anatomy of basal ganglia disorders," *Trends Neurosci.*, 1989, 12:366-375.

Anami et al., "Stepping stone sampling for retrieving artifactfree electroencephalogram during functional magnetic resonance imaging," *Neuroimage*, 2003, 19:281-295.

Anderson et al., "Mechanisms of deep brain stimulation: an intracellular study in rat thalamus," *J Physiol.*, 2004 559:301-313.

Bakker and Qin, "Electrochemical sensors," *Anal Chem.*, 2006, 78:3965-3984.

Bar-Gad et al., "Complex locking rather than complete cessation of neuronal activity in the globus pallidus of a 1-methyl-4-phenyl-1,2,3,6-tetrahydropyridine-treated primate in response to pallidal microstimulation," *J Neurosci.*, 2004, 24:7410-7419.

Bath et al., "Subsecond Adsorption and Desorption of Dopamine at Carbon-Fiber Microelectrodes," *Anal. Chem.*, 2000, 72:5994-6002.

Baur et al., "Fast-scan voltammetry of biogenic amines," *Anal Chem.*, 1988, 60:1268-1272.

Bekar et al., "Adenosine is crucial for deep brain stimulation-mediated attenuation of tremor," *Nat. Med.*, 2008, 14:75-80.

Benabid et al., "Combined (thalamotomy and stimulation) stereotactic surgery of the VIM thalamic nucleus for bilateral Parkinson disease," *Appl Neurophysiol.*, 1987, 50:344-346.

Benabid, "Deep brain stimulation for Parkinson's disease," *Curr Opin Neurobiol.*, 2003, 13:696-706.

Benveniste, "Brain microdialysis," *J Neurochem.*, 1989, 52:1667-1679.

Bergman et al., "Pathophysiology of Parkinson's disease: from clinical neurology to basic neuroscience and back," *Mov. Disord.*, 2002, 17:S28-S40.

Bergman et al., "Reversal of experimental parkinsonism by lesions of the subthalamic nucleus," *Science*, 1990, 249:1436-1438.

Bergstrom and Garris, "Utility of a tripolar stimulating electrode for eliciting dopamine release in the rat striatum," *J Neurosci. Methods*, 1999, 87:201-208.

Beurrier et al., "High-frequency stimulation produces a transient blockade of voltage-gated currents in subthalamic neurons," *J Neurophysiol.*, 2001, 85:1351-1356.

Blagoev et al., "Modelling the magnetic signature of neuronal tissue," *NeuroImage*, 2007, 37:137-148.

Blaha and Phillips, "A critical assessment of electrochemical procedures applied to the measurement of dopamine and its metabolites during drug-induced and species-typical behaviours," *Behav. Pharmacol.*, 1996, 7:675-708.

Blaha and Winn, "Modulation of dopamine efflux in the striatum following cholinergic stimulation of the substantia nigra in intact and pedunculopontine tegmental nucleus-lesioned rats," *J. Neurosci.*, 1993, 13(3):1035-1044.

Blaha et al., "Modulation of Dopamine Efflux in the Nucleus Accumbens after Cholinergic Stimulation of the Ventral Tegmental Area in Intact, Pedunculopontine Tegmental Nucleus-Lesioned, and Laterodorsal Tegmental Nucleus-Lesioned Rats," *J. Neurosci.*, 1996, 16:714-722.

Blaha et al., "Striatal dopamine release evoked by subthalamic stimulation in intact and 6-0HDA-lesioned rats: Relevance to deep brain stimulation in Parkinson's Disease," In: P. E. M. Phillips, S. G. Sandberg, S. Ahn, A. G. Phillips (Eds.), Monitoring Molecules in Neuroscience. University of British Columbia, Vancouver, BC, 2008, pp. 395-397.

Bledsoe et al., "Development of the Wireless Instantaneous Neurotransmitter Concentration System for intraoperative neurochemical monitoring using fast-scan cyclic voltammetry," *J Neurosurg.*, 2009, 111(4):712-723.

Bledsoe et al., "MRI compatible stereotaxic head-frame and navigation software for research in pigs," *Neuroscience*, 2008, Program#/Poster#: 695.8/UU92, 2 pages.

Bonmassar et al., "Visual evoked potential (VEP) measured by simultaneous 64-channel EEG and 3T fMRI," *Neuroreport*, 1999, 10:1893-1897.

Borland and Michael, "An introduction to electrochemical methods in neuroscience," in Michael AC, Borland LM (ed): Electrochemical Methods for Neuroscience. Boca Raton: CRC Press, 2007, 10 pages.

Borland et al., "Voltammetric study of extracellular dopamine near microdialysis probes acutely implanted in the striatum of the anesthetized rat," *J Neurosci Methods*, 2005, 146:149-158.

Breit et al., "Deep brain stimulation," *Cell Tissue Res*, 2004, 318:275-288.

Brown and Pilitsis, "Motor cortex stimulation for central and neuropathic facial pain: a prospective study of 10 patients and observations of enhanced sensory and motor function during stimulation," *Neurosurg.*, 2005, 56:290-297; discussion 290-297.

Bruet et al., "High frequency stimulation of the subthalamic nucleus increases the extracellular contents of striatal dopamine in normal and partially dopaminergic denervated rats," *J Neuropathol Exp Neurol.*, 2001, 60:15-24.

Bruet et al., "Neurochemical mechanisms induced by high frequency stimulation of the subthalamic nucleus: increase of extracellular striatal glutamate and GABA in normal and hemiparkinsonian rats," *J Neuropathol Exp Neurol.*, 2003, 62:1228-1240.

(56) References Cited

OTHER PUBLICATIONS

Burmeister et al., "Advances in the in vivo detection of GABA using enzyme coated microelectrode arrays," in Phillips PEM, Sandberg SG, Ahn S, Phillips AG (ed): proceeding of the 12th international conference on In Vivo methods 2008. University of British Columbia, Vancouver, Canada. 2008, p. 111-113.
Burmeister et al., "Improved ceramic-based multisite microelectrode for rapid measurements of L-glutamate in the CNS," *J Neurosci Methods*, 2002, 119:163-171.
Busenbark et al., "Accuracy of reported family histories of essential tremor," *Neurology*, 1996, 47:264-265.
Cahill et al., "Microelectrodes for the measurement of catecholamines in biological systems," *Anal Chem.*, 1996, 68(18):3180-3186.
Carmichael et al., "Functional MRI with active, fully implanted, deep brain stimulation systems: Safety and experimental confounds," *NeuroImage*, 2007, 37:508-517.
Cavus et al., "Decreased hippocampal volume on MRI is associated with increased extracellular glutamate in epilepsy patients," *Epilepsia*, 2008, 49:1358-1366.
Cechova and Venton, "Transient adenosine efflux in the rat caudate-putamen," *J Neurochem.*, 2008, 105:1253-1263.
Chang et al., "Studies of the neural mechanisms of deep brain stimulation in rodent models of Parkinson's disease," *Neurosci Biobehav Rev.*, 2008, 32:352-366.
Chow et al., "Delay in vesicle fusion revealed by electrochemical monitoring of single secretory events in adrenal chromaffin cells," *Nature*, 1992, 356(6364):60-63.
Clapp-Lilly et al., "An ultrastructural analysis of tissue surrounding a microdialysis probe," *J Neurosci Methods*, 1999, 90:129-142.
Covey et al., "Monitoring subthalamic nucleus-evoked dopamine release in the striatum using fast-scan cyclic voltammetry in vivo," in P.E.M. Phillips (Eds), Monitoring Molecules in Neuroscience. University of British Columbia, Vancouver, BC, 2008, 398-400.
Crespi et al., "In vivo voltammetry: from wire to wireless measurements," *J Neurosci Methods*, 2004, 140(1-2):153-61.
Cumming et al., "Kinetics of the uptake and distribution of the dopamine D(2,3) agonist (R)-N-[1-(11)C]n-propylnorapomorphine in brain of healthy and MPTP-treated Gottingen miniature pigs," *Nucl Med Biol.*, 2003, 30:547-553.
Dale et al., "Listening to the brain: microelectrode biosensors for neurochemicals," *Trends Biotechnol.*, 2005, 23:420-428.
Dale et al., "Rapid adenosine release in the nucleus tractus solitarii during defense response in rats: real-time measurement in vivo," *J Physiol.*, 2002, 544(Pt 1):149-160.
Dall et al., "Quantitative [18F]fluorodopa/PET and histology of fetal mesencephalic dopaminergic grafts to the striatum of MPTP-poisoned minipigs," *Cell Transplant.*, 2002, 11:733-746.
Danielsen et al., "The DaNeX study of embryonic mesencephalic, dopaminergic tissue grafted to a minipig model of Parkinson's disease: preliminary findings of effect of MPTP poisoning on striatal dopaminergic markers," *Cell Transplant.*, 2000, 9:247-259.
Dobbing, "The influence of early nutrition on the development and myelination of the brain," *Proc Royal Soc Lond B Biol Sci.*, 1964, 159:503-509.
Dommett et al., "How visual stimuli activate dopaminergic neurons at short latency," *Science*, 2005, 307:1476-1479.
Dostrovsky et al., "Microstimulation-induced inhibition of neuronal firing in human globus pallidus," *J Neurophysiol.*, 2000, 84:570-574.
Dugast et al., "Continuous in vivo monitoring of evoked dopamine release in the rat nucleus accumbens by amperometry," *Neuroscience*, 1994, 62:647-654.
Dunn et al., "Functional Brian Mapping at 9.4T Using a New MRI-Compatible Electrode Chronically Implanted in Rats," *Magnetic Resonance Med.*, 2009, 61:222-228.
Fedele et al., "Microdialysis in Parkinsonian patient basal ganglia: acute apomorphine-induced clinical and electrophysiological effects not paralleled by changes in the release of neuroactive amino acids," *Exp Neurol.*, 2001, 167:356-365.

Felix et al., "Stereotaxic atlas of the pig brain," *Brain Res Bull.*, 1999, 49:1-137.
Forster and Blaha, "Pedunculopontine tegmental stimulation evokes striatal dopamine efflux by activation of acetylocholine and glutamate receptors in the midbrain and pons of the rat," *Eur. J. Neurosci.*, 2003, 17:751-762.
Frank et al., "Hold your horses: impulsivity, deep brain stimulation, and medication in parkinsonism," *Science*, 2007, 318:1309-1312.
Garcia et al., "Dual effect of high-frequency stimulation on subthalamic neuron activity," *J Neurosci.*, 2003, 23:8743-8751.
Garcia et al., "High-frequency stimulation in Parkinson's disease: more or less?" *Trends Neurosci.*, 2005, 28:209-216.
Garguilo and Michael, "Amperometric microsensors for monitoring choline in the extracellular fluid of brain," *J Neurosci Methods*, 1996, 70:73-82.
Garris et al., "Dissociation of dopamine release in the nucleus accumbens from intracranial self-stimulation," *Nature*, 1999, 398(6722):67-9.
Garris et al., "Dopamine release and uptake both decrease in the partially denervated striatum in proportion to the loss of dopamine terminals," *Brain Res.*, 1997, 753(2):225-34.
Garris et al., "In vivo voltammetry with telemetry," in Michael AC, Borland LM (ed): Electrochemical Methods for Neuroscience. Boca Rhaton: CRC Press, 2007, pp. 233-259.
Garris et al., "Real-time measurement of electrically evoked extracellular dopamine in the striatum of freely moving rats," *J Neurochem.*, 1997, 68:152-161.
Garris et al., "Wireless transmission of fast-scan cyclic voltammetry at a carbon-fiber microelectrode: proof of principle," *J Neurosci Methods*, 2004, 140(1-2):103-115.
Gerhardt, "Rapid chronocoulometric measurements of norepinephrine overflow and clearance in CNS tissues," Neuromethods: voltammetric methods in brain systems, ed. G.B. A Boulton, RN Adams. 1995, Totowa, NJ: Human Press Inc. 117-51.
Gourine et al., "Adenosine release in nucleus tractus solitarii does not appear to mediate hypoxia-induced respiratory depression in rats," *J Physiol.*, 2002, 544:161-70.
Graybiel, "Neurotransmitters and neuromodulators in the basal ganglia," *Trends Neurosci*, 1990, 13:244-254.
Greene, "Deep-brain stimulation for generalized dystonia," *N Engl J Med*, 2005, 352:498-500.
Groh and Ney, "Anaethesia for magnetic resonance imaging," *Curr Opin Anaethesiol.*, 1997, 10:303-308.
Halassa et al., "Astrocytic Modulation of Sleep Homeostasis and Cognitive Consequences of Sleep Loss," *Neuron*, 2009, 61:213-219.
Hardesty and Sackeim, "Deep brain stimulation in movement and psychiatric disorders," *Biol Psychiatry*, 2007, 61:831-835.
Hardman et al., "Comparison of the Basal Ganglia in Rats, Marmosets, Macaques, Baboons, and Humans: Volume and Neuronal Number for the Output, Internal Relay and Striatal Modulating Nuclei," *J Camp. Neural.*, 2002, 445:238-255.
Hascup et al., "Determining the source of resting and physiologically-evoked L-glutamate levels using enzyme-based microelectrode arrays in awake rats," in Phillips PEM, Sandberg SG, Ahn S, Phillips AG (ed): proceeding of the 12th international conference on in vivo methods 2008. University of British Columbia, Vancouver, Canada. 2008, pp. 164-167.
Hascup et al., "Second-by second measures of L-glutamate and other neurotransmitter using enzyme based microelectrode arrays," in Micheal AC, Borland LM (ed): Electrochemical methods for neuroscience. CRC. 2006, 47 pages.
Henderson and Lad, "Motor cortex stimulation and neuropathic facial pain," *Neurosurg Focus*, 2006, 21:E6, 4 pages.
Herzog et al., "Most effective stimulation site in subthalamic deep brain stimulation for Parkinson's disease," *Mov. Disord.*, 2004, 19:1050-1054.
Hilker et al., "Deep brain stimulation of the subthalamic nucleus does not increase the striatal dopamine concentration in parkinsonian humans," *Mov Disord*, 2003, 18:41-48.
Hinzman et al., "Alterations in glutamate neurotransmission after traumatic brain injury: Study using enzyme-based microelectrode arrays," in Phillips PEM, Sandberg SG, Ahn S, Phillips AG (ed):

(56) References Cited

OTHER PUBLICATIONS proceeding of the 12th international conference on in vivo methods 2008. University of British Columbia, Vancouver, Canada. 2008, p. 372-374.
Hubble et al., "Deep brain stimulation for essential tremor," *Neurol.*, 1996, 46:1150-1153.
Huffman and Venton, "Carbon-fiber microelectrodes for in vivo applications," *Analyst.*, 2009, 134:18-24.
Hurley et al., "What has been learnt from study of dopamine receptors in Parkinson's disease?" *Pharmacol. Ther.*, 2002, 111:715-728.
Hyland et al., "Firing modes of midbrain dopamine cells in the freely moving rat," *Neurosci.*, 2002, 114:475-492.
Jackson et al., "Fast-scan cyclic voltammetry of 5-hydroxytryptamine," *Anal Chem.*, 1995, 67:1115-1120.
Jaquins-Gerstl and Michael, "Comparison of the brain penetration injury associated with microdialysis and voltammetry," *J Neurosci Methods*, 2009, 183:127-135.
Justice et al., "Voltammetry in the neuroscience," Clifton, NJ. Humana Press, 1987, 395 pages.
Kagohashi et al., "Wireless voltammetry recording in unanesthetised behaving rats," *Neurosci Res.*, 2008, 60:120-127.
Kawagoe et al., "pH-Dependent processes at Nafion-coated carbon-fiber microelectrodes," *J Electroanal Chem.*, 1993, 359:193-197.
Keeler et al., "Accessory equipment considerations with respect to MRI compatibility," *J Magn Reson Imaging*, 1998, 8:12-18.
Kern and Kumar, "Deep brain stimulation," *Neurologist*, 2007, 13:237-252.
Kimble et al., "Wireless Instantaneous Neurotransmitter Concentration Sensing System (WINCS) for Intraoperative Neurochemical Monitoring," $31^{st}$ *Annual International Conference of the IEEE EMBS*, 2009, 4 pages.
Kita and Kitai, "Efferent Projections of the Subthalamic Nucleus in the Rat: Light and Electron Microscopic Analysis with the PHA-L Method," *J Camp. Neural.*, 1987, 260:435-452.
Konradsson et al., "Second-by-second measurement of stimulated glutamate release and its modulation by α7 and mGlu 2/3 receptors: relevance to schizophrenia," in Phillips PEM, Sandberg SG, Ahn S, Phillips AG (ed): proceeding of the 12th international conference on in vivo methods 2008. University of British Columbia, Vancouver, Canada. 2008, pp. 123-126.
Krakow, "Imaging epileptic activity using functional MRI," *Neurodegener Dis*, 2008, 5:286-295.
Kristensen and Wightman, "Dispersion in flow injection analysis measured with microvoltammetric electrodes," *Anal Chem*, 1986, 58:986-988.
Kulagina et al., "Monitoring glutamate and ascorbate in the extracellular space of brain tissue with electrochemical microsensors," *Anal Chem.*, 1999, 71:5093-5100.
Lee et al, "Evolution of Deep Brain Stimulation: Human Electrometer and Smart Devices Supporting the Next Generation of Therapy," *Neuromodulation: Technology at the Neural Interface*, 2009, 12(2):85-103.
Lee et al., "Dopamine efflux in the rat striatum evoked by electrical stimulation of the subthalamic nucleus: potential mechanism of action in Parkinson's disease," *Eur. J. Neurosci.*, 2006, 23:1005-1014.
Lee et al., "High-frequency stimulation of the subthalamic nucleus increases glutamate in the subthalamic nucleus of rats as demonstrated by in vivo enzyme-linked glutamate sensor," *Brain Res.*, 2007, 1162:121-129.
Lee et al., "Neurotransmitter release from high-frequency stimulation of the subthalamic nucleus," *J Neurosurg.*, 2004, 101:511-517.
Lee et al., "Effect of High-Frequency Stimulation of the Subthalamic Nucleus on Subthalamic Neurons: An Intracellular Study," *Stereotactic. Funct. Neurasurg.*, 2003, 80:32-36.
Limberger et al., "'Real time' measurement of endogenous dopamine release during short trains of pulses in slices of rat neostriatum and nucleus accumbens: role of autoinhibition," *Naunyn-Schmiedeberg's Arch Pharmacol.*, 1991, 344:623-629.

Limousin et al., "Electrical stimulation of the subthalamic nucleus in advanced Parkinson's disease," *N Engl J Med*, 1998, 339:1105-1111.
Lind et al., "Mapping the amphetamine-evoked dopamine release in the brain of the Göttingen minipig," *Brain Res Bull.*, 2005, 65:1-9.
Lind et al., "The use of pigs in neuroscience: modeling brain disorders," *Neurosci Biobehav Rev*, 2007, 31(5):728-51.
Littlewood et al., "Mapping the central effects of ketamine in the rat using pharmacological MRI," *Psychopharmacology (Berl)*, 2006, 186:64-81.
Llaudet et al., "A three-enzyme microelectrode sensor for detecting purine release from central nervous system," *Biosens Bioelectron.*, 2003, 18:43-52.
Logothetis et al., "Neurophysiological investigation of the basis of the fMRI signal," *Nature*, 2001, 412:150-157.
Lowry and Fillenz, "Real-time monitoring of brain energy metabolism in vivo using microelectrochemical sensors: the effects of anesthesia," *Bioelectrochem.*, 2001, 54:39-47.
Lowry eta l., "An amperometric glucose-oxidase/poly(o-phenylenediamine) biosensor for monitoring brain extracellular glucose: in vivo characterization in the striatum of freely-moving rats," *J Neurosci Methods*, 1998, 79:65-74.
Lozano et al., "Subcallosal cingulate gyms deep brain stimulation for treatment-resistant depression," *Biol Psychiatry*, 2008, 64:461-467.
Maarrawi et al., "Motor cortex stimulation for pain control induces changes in the endogenous opioid system," *Neurol.*, 2007, 69:827-834.
Macmillan et al., "Accuracy of a miniature intracranial pressure monitor, its function during magnetic resonance scanning, and assessment of image artifact generation," *Neurosurgery*, 1999, 45:188-192.
Mandelkow et al., "Synchronization facilitates removal of MRI artefacts from concurrent EEG recordings and increases usable bandwidth," *Neuroimage*, 2006, 32-1120-1126.
Mayberg et al., "Deep brain stimulation for treatment-resistant depression," *Neuron*, 2005, 45:651- 660.
Mazzone et al., "Implantation of human pedunculopontine nucleus: a safe and clinically relevant target in Parkinson's disease," *Neuroreport*, 2005, 16:1877-1881.
McIntyre et al., "Uncovering the mechanism(s) of action of deep brain stimulation: activation, inhibition, or both," *Clin Neurophysiol.*, 2004, 115:1239-1248.
Meissner et al., "Deep brain stimulation in late stage Parkinson's disease: a retrospective cost analysis in Germany," *J Neurol.* 2005, 252:218-223.
Meissner et al., "Deep brain stimulation of subthalamic neurons increases striatal dopamine metabolism and induces contralateral circling in freely moving 6-hydroxydopamine-lesioned rats," *Neurosci Lett.*, 2002, 328:105-108.
Meissner et al., "Striatal dopaminergic metabolism is increased by deep brain stimulation of the subthalamic nucleus in 6-hydroxydopamine lesioned rats," *Neurosci Lett.*, 2001, 303:165-168.
Meltzer et al., "Modulation of dopamine neuronal activity by glutamate receptor subtypes," *Neurosci. Biobehav. Rev.*, 1997, 21:511-518.
Menon et al., "Combined event-related fMRI and EEG evidence for temporal-parietal cortex activation during target detection," *Neuroreport*, 1997, 8:3029-3037.
Michael et al., "Improving data acquisition for fast-scan cyclic voltammetry," *Anal Chem.*, 1999, 71(18):3941-3947.
Mikkelsen et al., "MPTP-induced Parkinsonism in minipigs: A behavioral, biochemical, and histological study," *Neurotoxicol Teratol*, 1999, 21(2):169-75.
Mitchell, "Acetylcholine and choline amperometric enzyme sensors characterized in vitro and in vivo," *Anal Chem.*, 2004, 76:1098-106.
Molina et al., "Additive Differential pulse voltammetry, instead of double differential pulse voltammetry," *Electrochem. Commun.*, 2001, 3:324-329.
Molinuevo et al., "Levodopa withdrawal after bilateral subthalamic nucleus stimulation in advanced Parkinson disease," *Arch Neurol.*, 2000, 57:983-988.

(56) References Cited

OTHER PUBLICATIONS

Moro et al., "Chronic subthalamic nucleus stimulation reduces medication requirements in Parkinson's disease," *Neurol.*, 1999, 53:85-90.
Moro et al., "The Impact on Parkinson's disease of electrical parameter settings in STN stimulation," *Neurology*, 2002, 59:706-713.
Moyer et al., "Effects of dopaminergic modulation on the integrative properties of the ventral striatal medium spiny neuron," *J Neurophysiol.*, 2007, 98:3731-3748.
Nandi et al., "Exploration of the role of the upper brainstem in motor control," *Stereotact Funct Neurosurg*, 2002, 78(3-4):158-167.
Naylor et al., "A new technique for the simultaneous recording of electroencephalograph activity and CNS biosensor data," in Phillips PEM, Sandberg SG, Ahn S, Phillips AG (ed): proceeding of the 12th international conference on in vivo methods 2008. University of British Columbia, Vancouver, Canada. 2008, pp. 127-129.
Netchiporouk et al., "Brain extracellular glucose assessed by voltammetry throughout the rat sleep-wake cycle," *Eur J Neurosci.*, 2001, 13:1429-1434.
Niazy et al., "Removal of FMRI environment artifacts from EEG data using optimal basis sets," *Neuroimage*, 2005, 28:720-737.
Nomoto et al., "The metabolic rate and vulnerability of dopaminergic neurons, and adenosine dynamics in the cerebral cortex, nucleus accumbens, caudate nucleus, and putamen of the common marmoset," *J Neural.*, 2000, 247:16-22.
Norris, "Principles of magnetic resonance assessment of brain function," *J Magn Reson Imaging*, 2006, 23:794-807.
Patel et al., "Unilateral subthalamotomy in the treatment of Parkinson's disease," *Brain*, 2003, 126:1136-1145.
Paul et al., "High frequency stimulation of the subthalamic nucleus influences striatal dopaminergic metabolism in the naive rat," *Neuroreport*, 2000, 11:441-444.
Perea and Araque, "Astrocytes potentiate transmitter release at single hippocampal synapses," *Science*, 2007, 317:1083-1086.
Phillips et al., "Parkinson disease: pattern of functional MR imaging activation during deep brain stimulation of subthalamic nucleus—initial experience," *Radiology*, 2006, 239:209-216.
Pohlmeyer et al., "Toward the Restoration of Hand Use to a Paralyzed Monkey: Brain-Controlled Functional Electrical Stimulation of Forearm Muscles," *PLoS ONE*, 2009, 4(6):1-8.
Pomerleau et al., "Real time in vivo measures of L-glutamate in the rat central nervous system using ceramic-based multisite microelectrode arrays," *Ann N Y Acad Sci.*, 2003, 1003:454-7.
Priori et al., "Do intraoperative microrecordings improve subthalamic nucleus targeting in stereotactic neurosurgery for Parkinson's disease?" *J Neurosurg Sci.*, 2003, 47:56-60.
Purdon et al., "An open-source hardware and software system for acquisition and real-time processing of electrophysiology during high field MRI," *J Neurosci Methods*, 2008, 175:165-186.
Purdon et al., "Simultaneous electroencephalography and functional magnetic resonance imaging of general anesthesia," *Ann N Y Acad Sci.*, 2009, 1157:61-70.
Rehncrona et al., "Long-term efficacy of thalamic deep brain stimulation for tremor: double-blind assessments," *Mov Disord.*, 2003, 18:163-170.
Ren et al., "Dopaminergic response to graded dopamine concentration elicited by four amphetamine doses," *Synapse*, 2009, 63:764-772.
Roberts and Mikulis, "Neuro MR: principles," *J Magn Reson Imaging*, 2007, 26:823-837.
Robinson et al., "Monitoring rapid chemical communication in the brain," *Chem Rev.*, 2008, 108:2554-2584.
Robinson et al., "Detecting Subsecond Dopamine Release with Fast-Scan Cyclic Voltammetry in Vivo," *Clin. Chem.*, 2003, 49:1763-1773.
Roham et al., "Diamond microelectrodes and CMOS microelectronics for wireless transmission of fast-scan cyclic voltammetry," *Conf Proc IEEE Eng Med Biol Soc*, 2007. 2007::6044-7.

Saint-Cyr et al., "Localization of clinically effective stimulating electrodes in the human subthalamic nucleus on magnetic resonance imaging," *J. Neurosurg.*, 2002, 97:1152-1166.
Sandberg and Garris, "Neurochemistry of addiction: monitoring essential neurotransmitters of addiction," in Koob GF, Kuhn C (ed): Novel Approaches to Addiction Boca Raton: CRC Press, 2010, 30 pages.
Saunders et al., "Microdialysis in nonhuman Primates," *Curr Protoc Neurosci*, 2001, Chapter 7:Unit7, 20 pages.
Schwarz et al., "Concurrent pharmacological MRI and in situ microdialysis of cocaine reveal relationship between the central hemodynamic response and local dopamine concentration," *Neuroimage*, 2004, 23:296-304.
Shastry, "Parkinson disease: etiology, pathogenesis and future of gene therapy," *Neurosci. Res.*, 2001, 41:5-12.
Shimo and Wichmann, "Neuronal activity in the subthalamic nucleus modulates the release of dopamine in the monkey striatum," *Eur. J Neurosci.*, 2009, 29:104-113.
Shon et al., "Comonitoring of adenosine and dopamine using the Wireless Instantaneous Neurotransmitter Concentration System: proof of principle: Laboratory investigation," *J Neurosurg.*, 2010, 112(3):539-548.
Stefurak et al., "Deep brain stimulation for Parkinson's disease dissociates mood and motor circuits: a functional MRI case study," *Mov Disord*, 2003, 18:1508-1516.
Suaud-Chagny et al., "Uptake of dopamine released by impulse flow in the rat mesolimbic and striatal systems in vivo," *J Neurochem.*, 1995, 65:2603-2611.
Suaud-Chagny, "In vivo monitoring of dopamine overflow in the central nervous system by amperometric techniques combined with carbon fibre electrodes," *Methods.*, 2004, 33:322-329.
Swamy et al., "Subsecond Detection of Physiological Adenosine Concentrations Using Fast-Scan Cyclic Voltammetry," *Anal. Chem.*, 2007, 79:744-750.
Tawfik et al., "Deep Brain Stimulation Results in Local Glutamate and Adenosine Release Investigation into the Role of Astrocytes," *Neurosurgery*, 2010, 67:367-75.
Thobois et al., "Chronic subthalamic nucleus stimulation and striatal D2 dopamine receptors in Parkinson's disease—A [(11)C]-raclopride PET study," *J Neurol.*, 2003, 250:1219-1223.
Tsubokawa et al., "Chronic motor cortex stimulation for the treatment of central pain," *Acta Neurochir Suppl (Wien)*, 1991, 52:137-139.
Tsubokawa et al., "Chronic motor cortex stimulation in patients with thalamic pain," *J Neurosurg.*, 1993, 78:393-401.
van der Zeyden et al., "Microdialysis of GABA and glutamate: analysis, interpretation and comparison with microsensors," *Pharmacol Biochem Behav.*, 2008, 90:135-147.
Venton et al., "Real-time decoding of dopamine concentration changes in the caudate-putamen during tonic and phasic firing," *J Neurochem*, 2003, 87:1284-1295.
Voges et al., "Bilateral high-frequency stimulation in the subthalamic nucleus for the treatment of Parkinson disease: correlation of therapeutic effect with anatomical electrode position," *J. Neurosurg.*, 2002, 96:269-279.
Volkmann, "Deep brain stimulation for the treatment of Parkinson's disease," *J Clin Neurophysiol.*, 2004, 21:6-17.
Watson et al., "In vivo measurements of neurotransmitters by microdialysis sampling," *Anal Chem*, 2006, 78:1391-1399.
Welter et al., "Effects of high-frequency stimulation on subthalamic neuronal activity in parkinsonian patients," *Arch Neurol.*, 2004, 61:89-96.
Wiedemann et al., "Strategies for Low Detection Limit Measurements with Cyclic Voltammetry," *Anal. Chem.*, 1991, 63:2965-2970.
Wightman et al., "Temporally resolved catecholamine spikes correspond to single vesicle release from individual chromaffin cells," *Proc Natl Acad Sci USA*, 1991, 88:10754-10758.
Williams and Millar, "Concentration-dependent actions of stimulated dopamine release on neuronal activity in rat striatum," *Neuroscience*, 1990, 39(1):1-16.

(56) References Cited

OTHER PUBLICATIONS

Williams and Millar, "Differential Actions of Endogenous and Iontophoretic Dopamine in Rat Striatum," *Eur J Neurosci*, 1990, 2(7):658-661.
Wilson and Gifford, "Biosensors for real-time in vivo measurements," *Biosens Bioelectron.*, 2005, 20:2388-2403.
Windels et al., "Effects of high frequency stimulation of subthalamic nucleus on extracellular glutamate and GABA in substantia nigra and globus pallidus in the normal rat," *Eur J Neurosci.*, 2000, 12:4141-4146.
Wu et al., "Determination of release and uptake parameters from electrically evoked dopamine dynamics measured by real-time voltammetry," *J Neurosci Methods*, 2001, 112:119-133.
Zhao et al., "Long term high frequency stimulation of STN increases dopamine in the corpus striatum of hemiparkinsonian rhesus monkey," *Brain Res.*, 2009, 1286:230-238.
Office Action in U.S. Appl. No. 13/392,387, mailed Jul. 13, 2016, 19 pages.
Office Action in U.S. Appl. No. 14/760,011, dated Jun. 16, 2016, 8 pages.
International Preliminary Report on Patentability for PCT/US2014/050550, mailed Feb. 18, 2016, 6 pages.
U.S. Appl. No. 61/358,512, filed Jun. 25, 2010, 51 pages.
International Search Report and Written Opinion for PCT/US2014/10882, mailed Apr. 4, 2014, 12 pages.
International Search Report and Written Opinion for PCT/US2014/50550 mailed Nov. 20, 2014, 10 pages.
Office action in U.S. Appl. No. 13/392,387, mailed Sep. 29, 2015, 9 pages.
Office Action in U.S. Appl. No. 14/760,011, mailed Dec. 4, 2015, 9 pages.
International Preliminary Report on Patentability for PCT/US2014/010882, mailed Jul. 23, 2015, 6 pages.
Eccles et al., Pulse Cyclic Voltammetry.II. Flowing Solutions, *Canadian J Chem.*, 65(8):1795-1799, Aug. 1, 1987.
European Communication pursuant to Article 94(3) EPC, dated Mar. 6, 2017, 5 pages.
European Search Report in the European Application No. 14834533.3, dated Feb. 17, 2017, 4 pages.

\* cited by examiner

Conventional Cyclic Voltammetry (CV)

Paired Pulse Voltammetry (PPV)

DIFFERENTIATING ANALYTES DETECTED USING FAST SCAN CYCLIC VOLTAMMETRY

CROSS-REFERENCE TO RELATED APPLICATIONS

This application claims the benefit of priority to U.S. Provisional Application Ser. No. 61/510,366, filed Jul. 21, 2011. The disclosure of the prior application is considered part of (and is incorporated by reference in) the disclosure of this application.

BACKGROUND

1. Technical Field

This document relates to methods and materials involved in differentiating analytes detected using a fast scan cyclic voltammetry (FSCV) method. For example, this document relates to methods and materials for using paired pulse voltammetry (PPV) to discriminate analytes on the basis of their adsorption characteristics to an electrode (e.g., a carbon fiber electrode).

2. Background Information

Cyclic voltammetry (CV) is a type of potentiodynamic electrochemical measurement that can be used to evaluate the electrochemical properties of an analyte in solution. CV generally involves ramping the potential of a working electrode linearly versus time like linear sweep voltammetry. Unlike linear sweep voltammetry, which ends when it reaches a set potential, the working electrode's potential ramp in CV is inverted when it reaches a set potential. The inversion can happen multiple times during a single evaluation. The current at the working electrode can be plotted versus the applied voltage to give the cyclic voltammogram trace.

SUMMARY

This document provides methods and materials involved in differentiating analytes detected using a FSCV method. For example, this document provides methods and materials for using PPV to discriminate analytes on the basis of their adsorption characteristics to an electrode (e.g., a carbon fiber electrode). As described herein, PPV methods can be used to obtain differential information related to adsorption characteristics of multiple analytes or metabolites within a sample or testing environment (e.g., within the brain of a mammal) by controlling the electrical potential repetition cycle time using a device or system such as a wireless instantaneous neurotransmitter concentration system (WINCS). Using PPV as described herein can allow for improved estimation of specific analyte and metabolite concentrations in complex electrochemical environments.

In general, one aspect of this document features a method for assessing a concentration of an analyte present within an environment. The method comprises, or consists essentially of, (a) obtaining voltammetric data for a primary pulse and a secondary pulse of a binary waveform, (b) determining a primary voltammogram and a secondary voltammogram from the data, (c) determining a difference between one of the primary voltammogram and the secondary voltammogram, wherein the difference provides an indication about the concentration, and (d) providing information about the difference or the concentration for display to a user. The analyte can be a chemical capable of being measured by electrochemistry (e.g., dopamine or adenosine). The environment can be brain tissue in vivo. The environment can be human brain tissue in vivo. The repetition time of the binary waveform can be between 1 milliseconds and 5 seconds. The gap time between each pairing of the primary pulse and the secondary pulse can be between 10 $\mu$seconds and 2.5 seconds. The determining the difference can comprise subtracting the secondary voltammogram from the primary voltammogram.

In another aspect, this document features a method for assessing a concentration of an analyte present within an environment. The method comprises, or consists essentially of, (a) obtaining a primary voltammogram and a secondary voltammogram, wherein the primary voltammogram was determined from voltammetric data for a primary pulse of a binary waveform, and wherein the secondary voltammogram was determined from voltammetric data for a secondary pulse of the binary waveform, (b) determining a difference between the primary voltammogram and the secondary voltammogram, wherein the difference provides an indication about the concentration, and (c) providing information about the difference or the concentration for display to a user. The analyte can be a chemical capable of being measured by electrochemistry (e.g., dopamine or adenosine). The environment can be brain tissue in vivo. The environment can be human brain tissue in vivo. The repetition time of the binary waveform can be between 1 milliseconds and 5 seconds. The gap time between each pairing of the primary pulse and the secondary pulse can be between 10 $\mu$seconds and 2.5 seconds. The determining the difference can comprise subtracting the secondary voltammogram from the primary voltammogram.

In another aspect, this document features a computer-implemented method for assessing a concentration of an analyte within a sample. The method comprises, or consists essentially of, (a) determining, by a computing system, a difference between a primary voltammogram and a secondary voltammogram, wherein the difference provides an indication about the concentration, wherein the primary voltammogram was determined from voltammetric data for a primary pulse of a binary waveform, and wherein the secondary voltammogram was determined from voltammetric data for a secondary pulse of the binary waveform, and (b) providing information about the difference or the concentration for display to a user. The analyte can be a chemical capable of being measured by electrochemistry (e.g., dopamine or adenosine). The sample can be brain tissue. The sample can be human brain tissue. The repetition time of the binary waveform can be between 1 milliseconds and 5 seconds. The gap time between each pairing of the primary pulse and the secondary pulse can be between 10 $\mu$seconds and 2.5 seconds. The determining the difference can comprise subtracting the secondary voltammogram from the primary voltammogram.

In another aspect, this document features a computerized system for assessing a concentration of an analyte within a sample, comprising, or consisting essentially of, (a) a communication port configured to receive voltammetric data for a primary pulse and a secondary pulse of a binary waveform applied to the sample, (b) one or more computer-readable storage media having recorded thereon instructions that, when executed, determines: (i) a primary voltammogram and a secondary voltammogram from the data, and (ii) a difference between the primary voltammogram and the secondary voltammogram, wherein the difference provides an indication about the concentration of the analyte, and (c) a communication port configured to provide information about the difference or the concentration for display to a user. The analyte can be a chemical capable of being measured by electrochemistry (e.g., dopamine or adenosine). The sample can be brain tissue. The sample can be brain tissue within a human. The repetition time of the binary waveform can be between 1 milliseconds and 5 seconds. The gap time between each pairing of the primary pulse and the secondary pulse can be between 10 μseconds and 2.5 seconds. The difference can comprise a voltammogram determined by subtracting the secondary voltammogram from the primary voltammogram.

In another aspect, this document features a tangible, non-transitory computer program product comprising, or consisting essentially of, instructions that, when executed, determines: (a) a primary voltammogram from voltammetric data for a primary pulse of a binary waveform applied to an environment, (b) a secondary voltammogram from voltammetric data for a secondary pulse of the binary waveform, and (c) a difference between the primary voltammogram and the secondary voltammogram, wherein the difference provides an indication about a concentration of an analyte within the environment. The analyte can be a chemical capable of being measured by electrochemistry (e.g., dopamine or adenosine). The environment can be brain tissue in vivo. The environment can be brain tissue within a human. The repetition time of the binary waveform can be between 1 milliseconds and 5 seconds. The gap time between each pairing of the primary pulse and the secondary pulse can be between 10 μseconds and 2.5 seconds. The difference can be determined by subtracting the secondary voltammogram from the primary voltammogram.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials involved in differentiating analytes detected using a FSCV method. For example, this document provides methods and materials for using PPV to discriminate analytes based on their adsorption characteristics to an electrode (e.g., a carbon fiber electrode). As described herein, PPV can be used to assess a concentration of an analyte present within a tissue in vivo or in vitro. For example, the methods and materials provided herein can be used to assess the concentration of an analyte (e.g., a chemical such as a neurochemical or an ion) within brain tissue. In some cases, the methods and materials provided herein can be used to assess the concentration of an analyte during deep brain stimulation. Examples of analytes that can be detected using the methods and materials provided herein include, without limitation, ions such as calcium, magnesium, sodium, potassium, protons (pH), iron, copper, chromium, lead, mercury, cobolt, gold, lithium, cesium, barium, zinc, chloride, bicarbonate, phosphate, bromide, iodide, sulfide, oxide, sulfide, and fluoride and chemicals such as dopamine, serotonin, adenosine, adenine mono- or tri-phosphate, norepinephrine, GABA, histamine, acetylcholine, glutamate, aspartate, epinephrine, nitric oxide, glycine, trace amines (e.g., tryptamine, phenylethylamine, tyramine, and octopamine), and amino acid-based neuropeptides (e.g., endorphins, enkephalins, and vasopressin). For example, PPV can be used to assess the concentration of one or more chemicals (e.g., dopamine or adenosine).

Figure 1A:
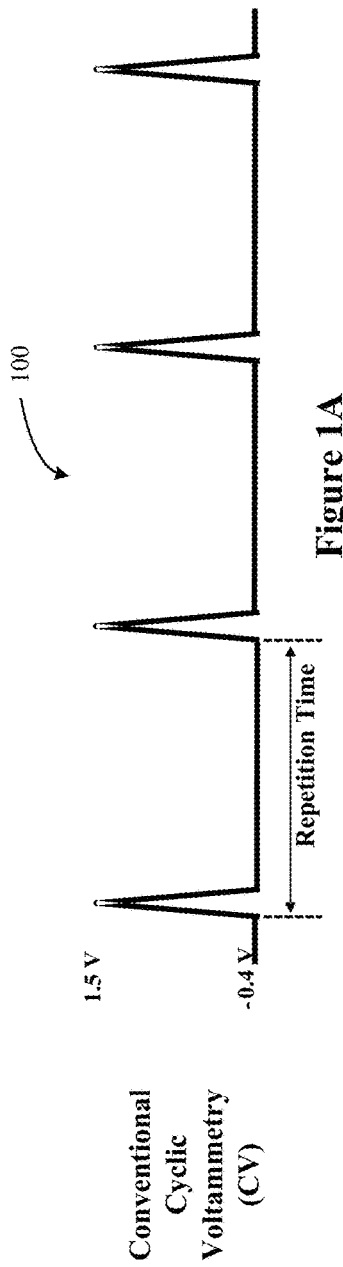
FIG. 1A is a diagram of a conventional FSCV waveform.
Figure 1B:
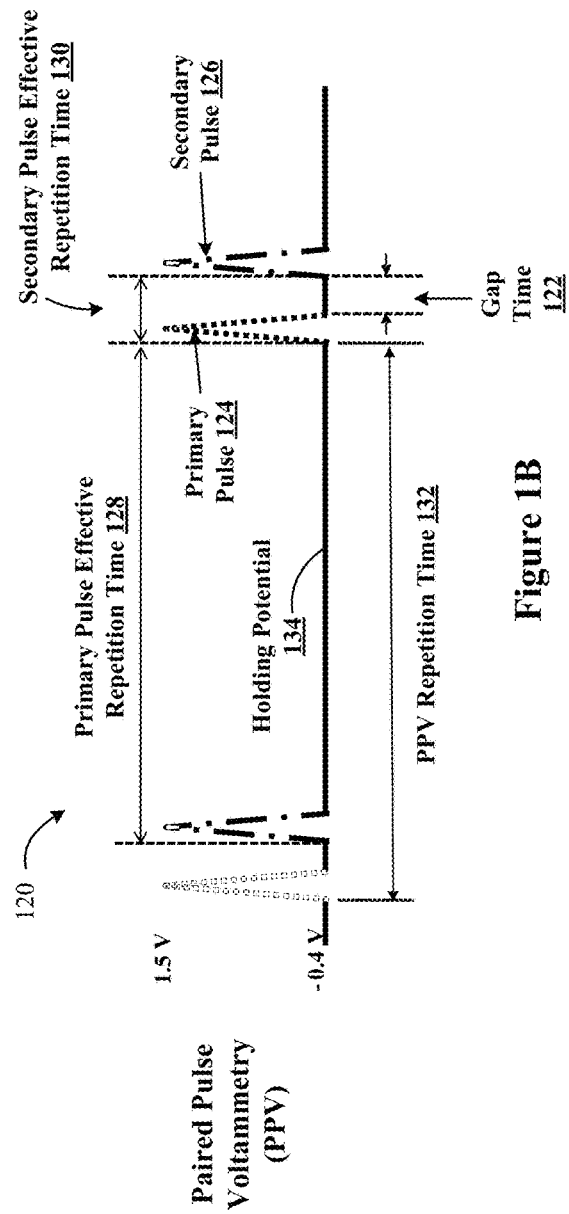
FIG. 1B is a diagram of an exemplary paired pulse voltammetry (PPV) waveform. This PPV waveform includes a selected binary waveform with a specific time gap between each of its two comprising pulses, such that each binary wave is repeated, while holding the working electrode at a constant potential between the waves. The primary pulse can have a long effective repetition time compared with the secondary pulse effective repetition time.

In some cases, the methods and materials provided herein can be used in a FSCV process to obtain voltammetric data for a primary pulse 124 and a secondary pulse 126 of a binary waveform (FIG. 1B). From this data, a primary voltammogram and a secondary voltammogram can be constructed. Once constructed, a difference between primary and secondary voltammograms indicative of the concentration of an analyte can be determined. For example, the secondary voltammogram can be subtracted from the primary voltammogram to create a difference voltammogram that provides an indication about the concentration of the analyte being assessed.

Any appropriate device with the ability to do variable timing of voltammetry can be used to obtain PPV data by applying a binary waveform to a tissue being assessed. For example, a WINCS device can be used to obtain voltammetric data pertaining to a tissue being assessed. In some cases, a voltammetry device can include one or more electrodes or sensors to detect one or more analytes. In some cases, a single electrode or sensor can be used to detect a single chemical. For example, a voltammetry device can include a first electrode designed to detect dopamine and a second electrode designed to detect glutamate. Another design uses a singular sensing electrode to detect different chemicals by applying different voltage ramps at slightly different times.

In some cases, a device (e.g., a WINCS device) can be implanted within a patient. For example, a WINCS device can be implanted within a patient's skull. In some cases, a device can include a single electrode for FSCV that contains two independent areas of active electrode such as pyrolytic carbon or carbon fiber. Then by varying the FSCV impressed voltage, signals representing different neurochemicals can be determined. If the active electrode areas are too close together, which would cause interference, the signals can be multiplexed such that the signal is detected quasi simultaneously by measuring one chemical directly after a preceding chemical. The device can also be used to determine the effect of stimulation. For example, stimulation of two different areas of the brain can produce a release of different neurochemicals (such as histamine, adenosine, glutamate, and dopamine). The ratio or absolute amount changes of the released neurochemicals can provide a physiologic effect of interest, such as creating long-term memory in patients with short-term memory loss.

In some cases, one or more chemicals (e.g., dopamine, adenosine, serotonin, and norepinephrine) can be detected using FSCV with various scan waveforms applied to one or more electrodes or sensors. The scan waveforms can be varied by manipulating physical aspects of the waveforms such as the peak voltage, voltage ramp, and repetition time.

When using PPV to assess the concentration of a particular analyte within a tissue in vivo, any appropriate PPV repetition time 132 and any appropriate gap time 122 of a binary waveform can be used (refer to FIG. 1B). For example, PPV repetition times ranging from about 30 milliseconds to about 1000 milliseconds (e.g., from about 30 milliseconds to about 750 milliseconds, from about 30 milliseconds to about 500 milliseconds, from about 30 milliseconds to about 250 milliseconds, from about 30 milliseconds to about 100 milliseconds, from about 40 milliseconds to about 1000 milliseconds, from about 50 milliseconds to about 1000 milliseconds, from about 100 milliseconds to about 1000 milliseconds, or from about 150 milliseconds to about 1000 milliseconds) and gap times ranging from about 1 millisecond to about 100 milliseconds (e.g., from about 1 millisecond to about 90 milliseconds, from about 1 millisecond to about 80 milliseconds, from about 1 millisecond to about 70 milliseconds, from about 2 millisecond to about 100 milliseconds, from about 3 millisecond to about 100 milliseconds, from about 5 millisecond to about 100 milliseconds, or from about 10 millisecond to about 100 milliseconds) can be used. Any appropriate form of pulse shape 124/126 can be used, such as a triangle shape pulse (FIG. 1B) or an N shape pulse.

Figure 7:
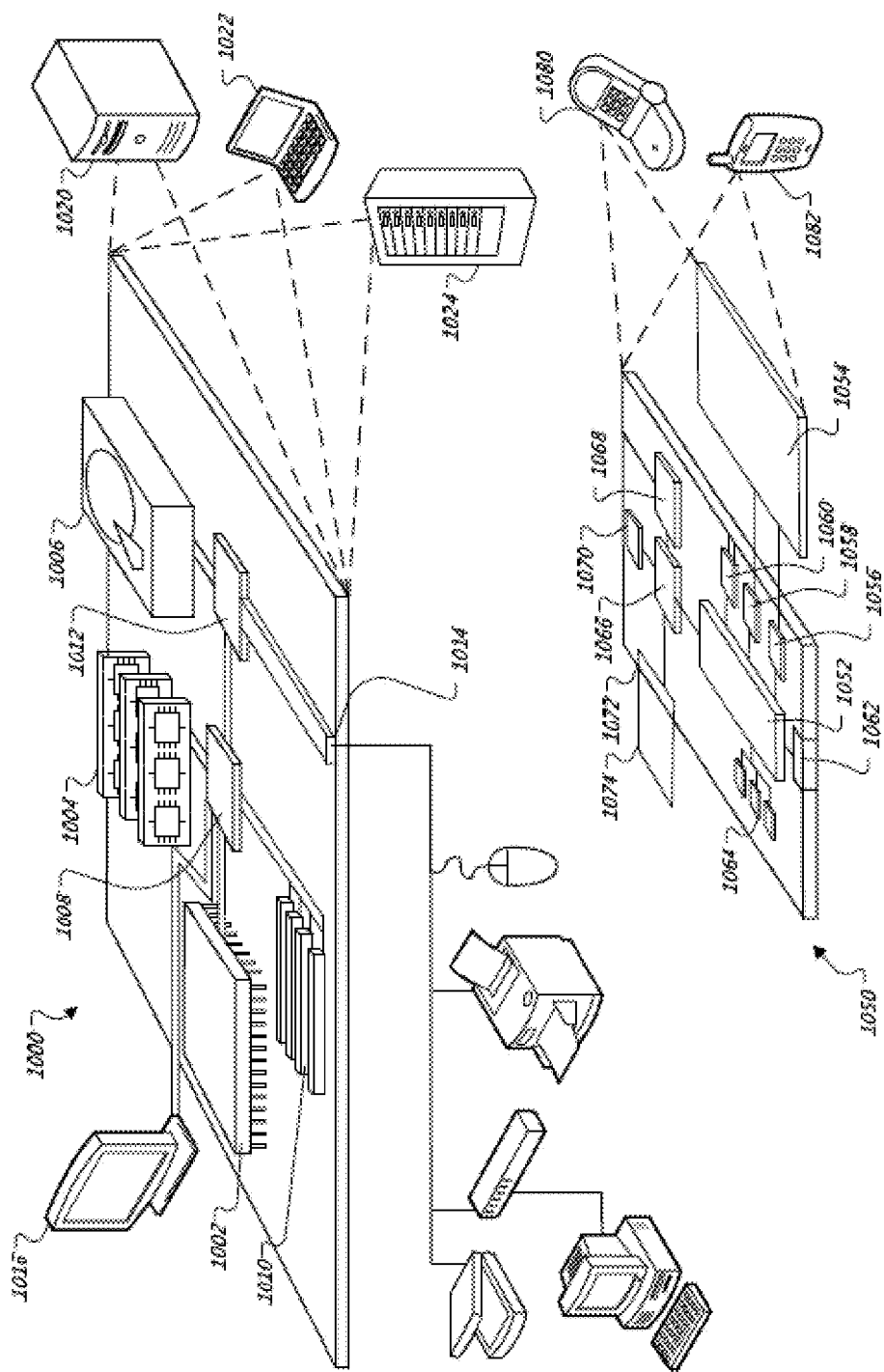
FIG. 7 is a block diagram of computing devices that may be used to implement the systems and methods described in this document, as either a client or as a server or plurality of servers.

FIG. 7 is a block diagram of computing devices 1000, 1050 that may be used to implement the systems and methods described herein, as either a client or as a server or plurality of servers. Computing device 1000 is intended to represent various forms of digital computers, such as laptops, desktops, workstations, personal digital assistants, servers, blade servers, mainframes, and other appropriate computers. Computing device 1050 is intended to represent various forms of mobile devices, such as personal digital assistants, cellular telephones, smartphones, and other similar computing devices. The components shown here, their connections and relationships, and their functions, are meant to be exemplary only, and are not meant to limit implementations described and/or claimed in this document.

Computing device 1000 includes a processor 1002, memory 1004, a storage device 1006, a high-speed interface 1008 connecting to memory 1004 and high-speed expansion ports 1010, and a low speed interface 1012 connecting to low speed bus 1014 and storage device 1006. Each of the components 1002, 1004, 1006, 1008, 1010, and 1012, are interconnected using various buses, and may be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as display 1016 coupled to high speed interface 1008. In other implementations, multiple processors and/or multiple buses may be used, as appropriate, along with multiple memories and types of memory. Also, multiple computing devices 1000 may be connected, with each device providing portions of the necessary operations (e.g., as a server bank, a group of blade servers, or a multi-processor system).

The memory 1004 stores information within the computing device 1000. In one implementation, the memory 1004 is a volatile memory unit or units. In another implementation, the memory 1004 is a non-volatile memory unit or units. The memory 1004 may also be another form of computer-readable medium, such as a magnetic or optical disk.

The storage device 1006 is capable of providing mass storage for the computing device 1000. In one implementation, the storage device 1006 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 1004, the storage device 1006, or memory on processor 1002.

The high speed controller 1008 manages bandwidth-intensive operations for the computing device 1000, while the low speed controller 1012 manages lower bandwidth-intensive operations. Such allocation of functions is exemplary only. In one implementation, the high-speed controller 1008 is coupled to memory 1004, display 1016 (e.g., through a graphics processor or accelerator), and to high-speed expansion ports 1010, which may accept various expansion cards (not shown). In the implementation, low-speed controller 1012 is coupled to storage device 1006 and low-speed expansion port 1014. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1000 may be implemented in a number of different forms, as shown in the figure. For example, it may be implemented as a standard server 1020, or multiple times in a group of such servers. It also may be implemented as part of a rack server system 1024. In addition, it may be implemented in a personal computer such as a laptop computer 1022. Alternatively, components from computing device 1000 may be combined with other components in a mobile device (not shown), such as device 1050. Each of such devices may contain one or more of computing device 1000, 1050, and an entire system may be made up of multiple computing devices 1000, 1050 communicating with each other.

Computing device 1050 includes a processor 1052, memory 1064, an input/output device such as a display 1054, a communication interface 1066, and a transceiver 1068, among other components. The device 1050 may also be provided with a storage device, such as a microdrive or other device, to provide additional storage. Each of the components 1050, 1052, 1064, 1054, 1066, and 1068, are interconnected using various buses, and several of the components may be mounted on a common motherboard or in other manners as appropriate.

The processor 1052 can execute instructions within the computing device 1050, including instructions stored in the memory 1064. The processor may be implemented as a chipset of chips that include separate and multiple analog and digital processors. Additionally, the processor may be implemented using any of a number of architectures. For example, the processor 410 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 1050, such as control of user interfaces, applications run by device 1050, and wireless communication by device 1050.

Processor 1052 may communicate with a user through control interface 1058 and display interface 1056 coupled to a display 1054. The display 1054 may be, for example, a TFT (Thin-Film-Transistor Liquid Crystal Display) display or an OLED (Organic Light Emitting Diode) display, or other appropriate display technology. The display interface 1056 may comprise appropriate circuitry for driving the display 1054 to present graphical and other information to a user. The control interface 1058 may receive commands from a user and convert them for submission to the processor 1052. In addition, an external interface 1062 may be provide in communication with processor 1052, so as to enable near area communication of device 1050 with other devices. External interface 1062 may provide, for example, for wired communication in some implementations, or for wireless communication in other implementations, and multiple interfaces may also be used.

The memory 1064 stores information within the computing device 1050. The memory 1064 can be implemented as one or more of a computer-readable medium or media, a volatile memory unit or units, or a non-volatile memory unit or units. Expansion memory 1074 may also be provided and connected to device 1050 through expansion interface 1072, which may include, for example, a SIMM (Single In Line Memory Module) card interface. Such expansion memory 1074 may provide extra storage space for device 1050, or may also store applications or other information for device 1050. Specifically, expansion memory 1074 may include instructions to carry out or supplement the processes described above, and may include secure information also. Thus, for example, expansion memory 1074 may be provide as a security module for device 1050, and may be programmed with instructions that permit secure use of device 1050. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 1064, expansion memory 1074, or memory on processor 1052 that may be received, for example, over transceiver 1068 or external interface 1062.

Device 1050 may communicate wirelessly through communication interface 1066, which may include digital signal processing circuitry where necessary. Communication interface 1066 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1068. In addition, short-range communication may occur, such as using a Bluetooth, WiFi, or other such transceiver (not shown).

Device 1050 may also communicate audibly using audio codec 1060, which may receive spoken information from a user and convert it to usable digital information. Audio codec 1060 may likewise generate audible sound for a user, such as through a speaker, e.g., in a handset of device 1050. Such sound may include sound from voice telephone calls, may include recorded sound (e.g., voice messages) and may also include sound generated by applications operating on device 1050.

The computing device 1050 may be implemented in a number of different forms, as shown in the figure. For example, it may be implemented as a cellular telephone 1080. It may also be implemented as part of a smartphone 1082, personal digital assistant, or other similar mobile device.

Additionally computing device 1000 or 1050 can include Universal Serial Bus (USB) flash drives. The USB flash drives may store operating systems and other applications. The USB flash drives can include input/output components, such as a wireless transmitter or USB connector that may be inserted into a USB port of another computing device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

The invention will be further described in the following examples, which do not limit the scope of the invention described in the claims.

EXAMPLES

Example 1—Paired Pulse Voltammetry (PPV) for Differentiating Complex Analytes Using a Wireless Instantaneous Neurotransmitter Concentration System (WINCS)

Since adsorption is a property specific to each analyte, adsorption could be a factor for discriminating various analytes in FSCV. The adsorption peak current ($i^a_p$) is known to follow the following equation (Bard and Faulkner, Electrochemical Methods: Fundamentals and Applications, New York, John Wiley & Sons, Inc., (2001)).

$$i_p^a = (9.39 \times 10^5) n^2 A v \Gamma_0 \qquad (1)$$

Where n is the number of electrons involved in electrode reaction, A is the electrode surface area, v is the sweep rate, and $\Gamma_0$ is the amount of adsorbed analyte. As described in the equation (1), adsorption current is linearly proportional to the amount of adsorbed analyte. If the time is sufficiently short and the analyte concentration is constant within that short time, the adsorption current will become a function of time. In FSCV, the time between cyclic voltage waveform pulses at which a constant potential is held (FIG. 1A) also affects the amplitude of a species that adsorbs to the electrode surface (Bath et al., *Analytical Chemistry*, 72:5994-6002 (2000)). The greater the time between scans, the more the adsorption processes is prone to occur—and to approach equilibrium. For a specific repetition time, analyte adsorption depends upon the intrinsic properties of the analyte, such as molecular mass and charge. Thus, the repetition time can be used for differentiating various analytes by utilizing the analytes' adsorption characteristics in FSCV.

Paired Pulse Voltammetry

The following describes the use of Paired Pulse Voltammetry (PPV) as a FSCV method to obtain differential information related to adsorption characteristics of analytes and metabolites by controlling the scan repetition time of a WINCS device.

The most widely used conventional FSCV waveform for the detection of adenosine and dopamine is a triangle shaped voltammetric pulse (FIG. 1A). Repeating 10 times per second, the applied potential sweeps from −0.4V to +1.5V and back to −0.4 V, at a voltage ramp rate of 400 V/s. The working electrode is held at a holding potential of −0.4V between voltammetric pulses.

Unlike conventional FSCV, PPV involves using a paired pulse (e.g., primary pulse 124 and secondary pulse 126). The primary pulse is defined as the first pulse of the binary waves, and the secondary pulse is defined as the following pulse (FIG. 1B). This binary waveform has a specific gap time 122 between the two pulses 124/126 of each binary wave. A negative holding potential 134 between the paired pulses/binary waves is used similarly to conventional FSCV.

The primary pulse effective repetition time 128 is the time lapse between the start of a primary pulse and the start of the secondary pulse of the previous binary waveform (FIG. 1B). The secondary pulse effective repetition time 130 is the time lapse between the start of a primary pulse 124 of a binary wave and the start of a secondary pulse 126 of the same binary wave. For example, if PPV is used with a PPV repetition time of 5 Hz (200 ms between two binary waveforms), a 400 V/s voltage ramp rate (9.8 ms per single pulse from −0.4V to 1.5V and back to −0.4V), and a 2.2 ms gap time between primary and second pulses of the binary waveform, then the primary pulse effective repetition time will be 188 ms (=200 ms−9.8 ms−2.2 ms), and the secondary pulse effective repetition time will be 12 ms (=9.8 ms+2.2 ms). The difference between two pulses reflects the amount of adsorbed analyte due to the discrepancy between the primary and secondary effective repetition times.

Figure 2A:
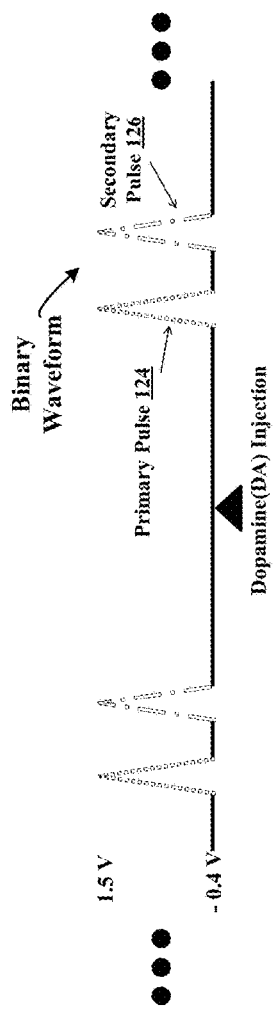
FIG. 2 is a diagram of data analysis using PPV techniques. Three types of voltammograms can be reconstructed using PPV. The primary voltammogram (P voltammogram) was constructed with the voltammetric data set acquired at the primary pulse of the binary waveform. The secondary voltammogram (S voltammogram) was constructed with the data set acquired from voltammetry at the second pulse of the binary waveform. The difference voltammogram (P-S voltammogram) was constructed by subtracting the S voltammogram from the P voltammogram.
Figure 2B:
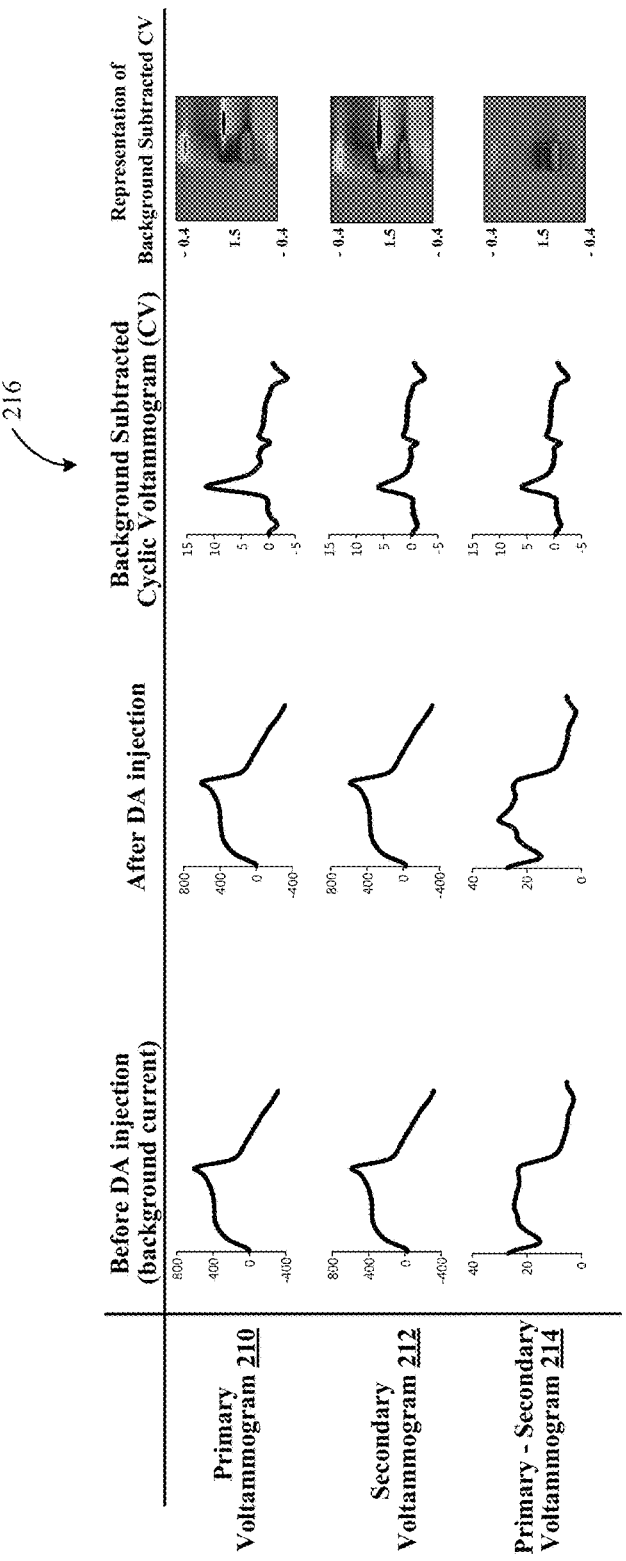

As illustrated in FIG. 2B, three types of voltammograms were reconstructed using PPV: (1) the primary voltammogram (P voltammogram) 210, constructed with the voltammetric data set acquired at the primary pulse of the binary waveform (2) the secondary voltammogram (S voltammogram) 212, constructed with the data set acquired from voltammetry at the secondary pulse of the binary waveform, and (3) the difference voltammogram (P-S voltammogram) 214, constructed by subtracting the S voltammogram from P voltammogram at each time point of data acquisition. In addition, three background subtracted cyclic voltammograms 216 were calculated by subtracting each subtraction background current obtained at the same time point.

Data Acquisition

All experiments were performed using a WINCS device, which is described elsewhere (Bledsoe et al., *J. Neurosurgery*, 111:712-23 (2009)) and Shon et al., *J. Neurosurgery*, 112:539-48 (2010)). The acquired data was displayed in several graphical formats for nearly real-time analysis by engineered software (WINCSware) running on the WINCS base station computer.

Electrodes

For FSCV, a carbon fiber microelectrode (CFM) was constructed by aspirating a single carbon fiber (d=7 μm) (Cytec Thornel® T300) into a borosilicate glass capillary and pulling to a microscopic tip using a pipette puller (P-2000, Sutter Instruments, CA, USA). The exposed carbon fiber was trimmed to a final length of ~100 μm using a scalpel (Cahill et al., *Analytical Chemistry*, 68:3180-6 (1996)). The Ag/AgCl reference electrode was fabricated by chloridizing a 31 gauge silver wire (Garris et al., *J. Neurochemistry*, 68:152-61 (1997)).

Flow Injection Apparatus

Flow injection analysis was used for in vitro measurements with FSCV at a CFM. In this procedure, well established for device testing and microsensor calibration, a CFM was placed in a flowing stream of buffer, and analyte was injected as a bolus. The buffer solution, composed of 150 mM sodium chloride and 12 mM Trizma base at pH 7.4, was pumped across the CFM at a rate of 2 mL/minute. An electronic loop injector, locally fabricated, introduced a bolus of analyte into the flowing stream at defined test concentrations.

Chemicals

Drugs were dissolved in distilled water at a stock concentration of 10 mM, diluted with flow injection analysis buffer. Adenosine and DA hydrochloride were purchased from Sigma Aldrich (St. Louis, Mo.).

In Vivo Experiments

Three adult male Sprague-Dawley rats, weighing 300 to 400 g, were used for the in vivo study. Rats were housed under standard conditions with ad libitum access to food and water.

Results

Paired Pulse Voltammetry for Dopamine, pH Changes, and Adenosine

PPV was applied to solutions of: (i) dopamine (DA) 1 μM, (ii) adenosine (ADO) 5 μM, and (iii) ΔpH+0.1. The PPV used the following parameters: −0.4V rest/holding potential, 1.5V peak potential, 400 V/s scan rate, 2.2 ms gap time, and 5 Hz repetition rate (200 ms PPV repetition time). The primary pulse effective repetition time was 188 ms (=200 ms−9.8 ms−2.2 ms), and the secondary pulse effective repetition time was 12 ms (=9.8 ms+2.2 ms).

Figure 3:
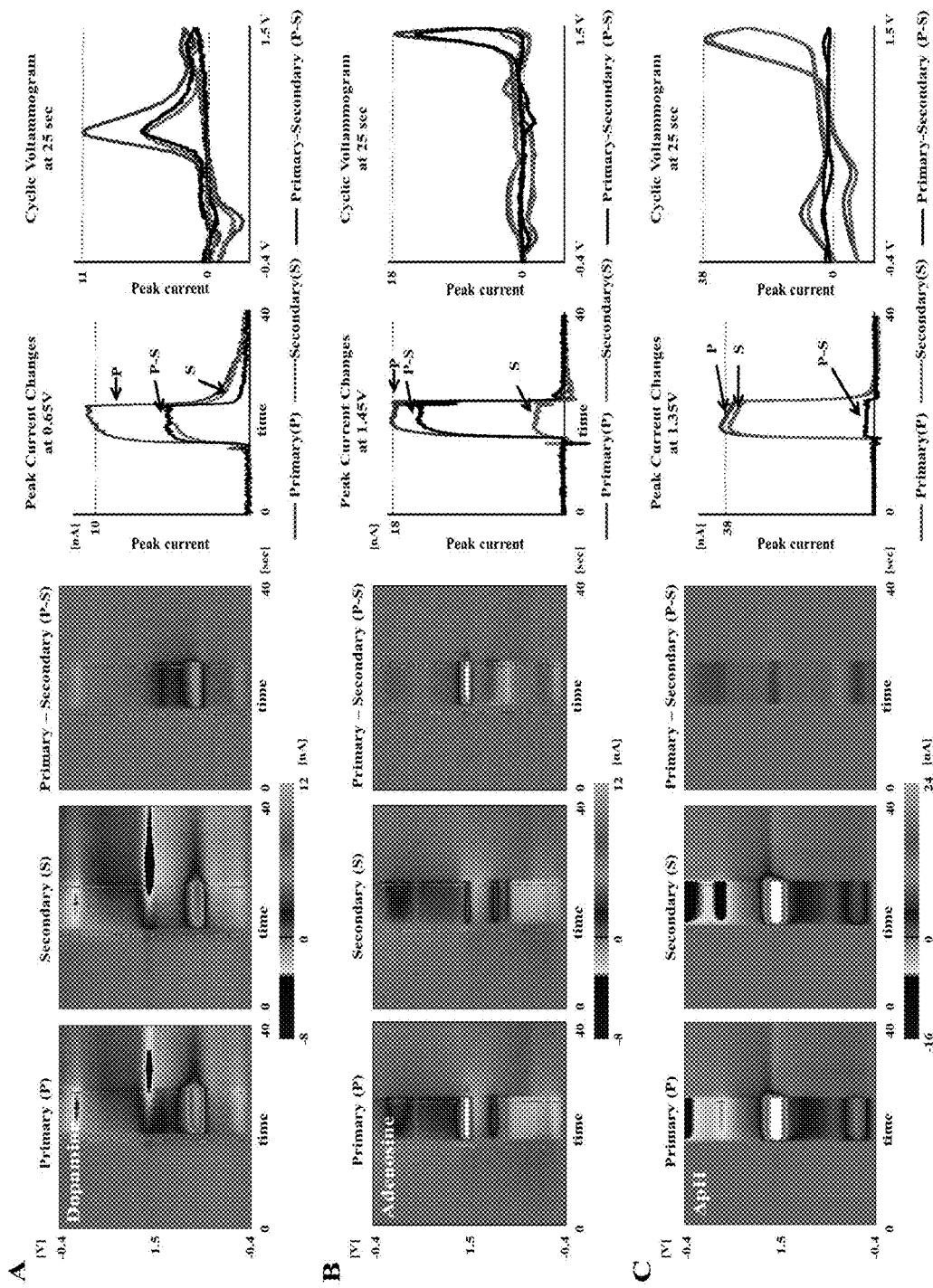
FIG. 3 contains data from the analysis of (A) dopamine (DA), (B) adenosine, and (C) ΔpH responses in PPV using flow injection analysis. The three pseudo-color plots for each of the panels (A)-(C) consist of a P voltammogram, a S voltammogram, and their difference in PPV. Panel A shows PPV responses to DA 1 μM. The peak current of the background subtracted S voltammogram at 0.6 V potential had decreased by approximately 50% when compared to the background subtracted P voltammogram. Panel B shows PPV responses to adenosine 5 μM. The first oxidation current of S voltammogram at 1.35V decreased up to 80% compared to S voltammogram, which lead to clear current changes in the P-S voltammogram. Panel C shows PPV responses to 0.1 ΔpH. The P voltammogram and S voltammogram of pH change were very similar to each other, such that only a small amount of signal change was noticeable in the P-S voltammogram.

For DA, the P-S voltammogram exhibited a clear DA signal, presumably since catecholamines like DA tend to be adsorbed on the CFM surface under a negative holding potential and are more dependent on effective repetition time when compared to the smaller $H^+$ ions (FIG. 3; panel A). The peak current of the background subtracted S voltammogram at 0.6 V potential had decreased by approximately 50% when compared to the background subtracted P voltammogram. The background subtracted P-S voltammogram therefore exhibited a clear DA signal at the same potential. An interesting result was that the changes occurring at the reduction potential around −0.2V seemed to be unnoticeable in the P-S voltammogram. This could be explained by the two different sources of current changes and their time dependence. The oxidation current changes were from the DA getting adsorbed on the CFM surface during the gap time (e.g., "holding time") between each triangular pulse/the effective repetition time, whereas the source of reduction current is DA-o-quinone formed at the CFM surface, just after DA oxidation at 0.6V in an anodic sweep, and is unlikely to be significantly influenced by the repetition time.

The first oxidative peak current of adenosine, occurring at 1.35V, decreased by up to 80% in the S voltammogram when compared to the P voltammogram (FIG. 3; panel B). It resulted in clearer difference signal in the P-S voltammogram. Although DA was well known for adsorption at carbon surface during a −0.4V holding potential, the comparison of difference (P-S) voltammograms between DA and ADO revealed that ADO had a larger difference signal than DA. A possible explanation was that the difference signal may come from not how well but how fast the molecules were adsorbed at CFM surface due to diffusional limitations of mass transport. The slower diffusion and adsorption of ADO compared to DA may lead to smaller amounts of adenosine adsorption during the given effective repetition time of the secondary voltammogram and thus resulting in smaller current. Another interesting finding was that the second peak oxidation current of ADO at 1.2V was nearly the same between the P and S voltammograms, similar to the reduction currents of DA at −0.2 V. A similar explanation was proposed assuming that the second oxidation peak current, arising from the adenosine already adsorbed at the CFM surface was unlikely to be influenced by the effective repetition time.

PPV responses to pH changes exhibited a different pattern than that of both DA and ADO (FIG. 3; panel C). The Primary and secondary voltammograms were very similar, such that only a small amount of signal change was noticeable in the P-S voltammogram. This may be due to the high mobility and thus faster adsorption of the H+ ions to the CFM, quick enough to adsorb to near saturation even with the comparatively short repetition time of the secondary voltammetry.

Effect of Repetition Time on PPV

Figure 4:
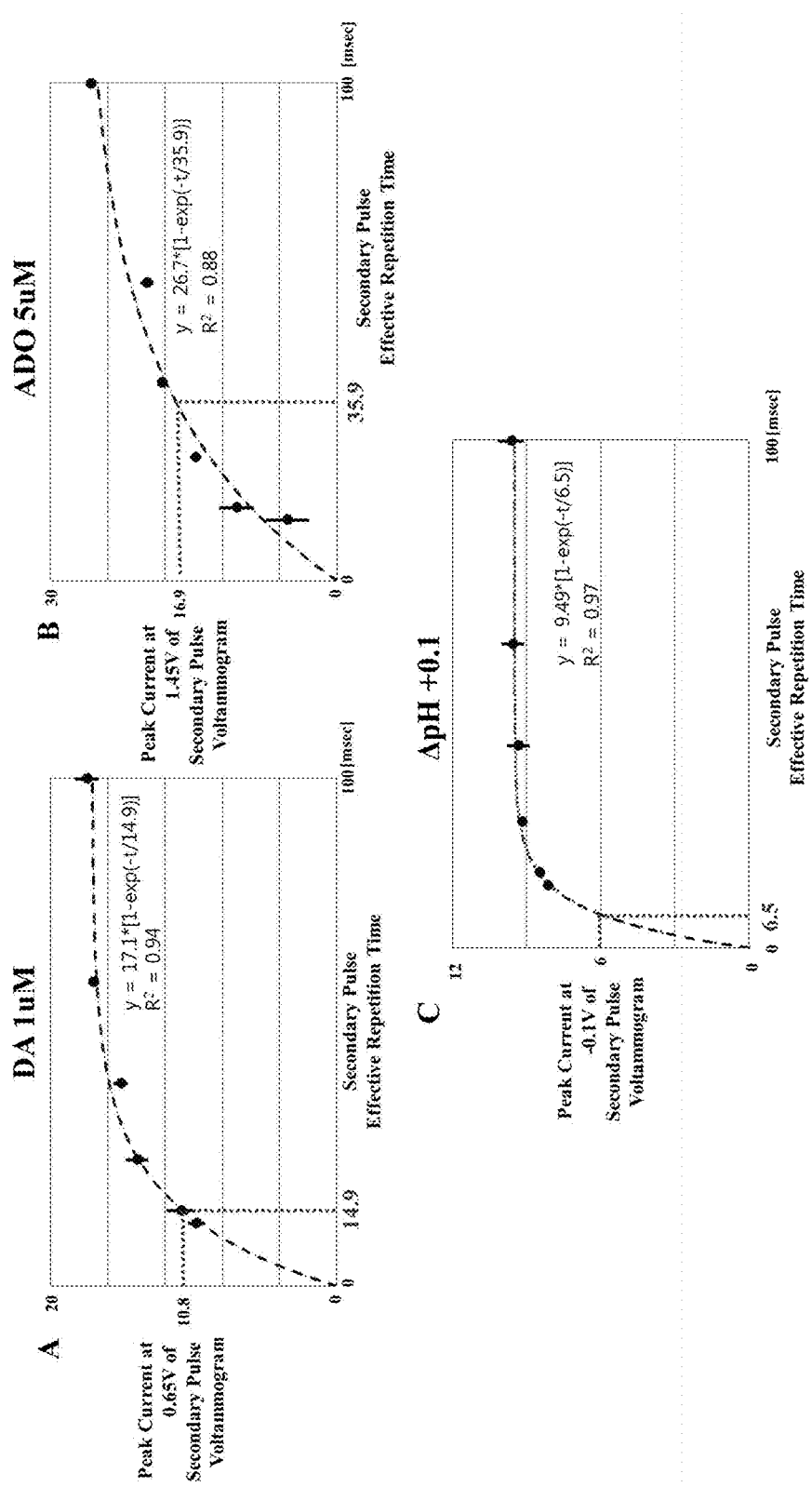
FIG. 4 contains three graphs plotting the effect of secondary pulse effective repetition time on PPV. Panel A contains a graph plotting DA peak currents at 0.65V from the S voltammogram using six secondary pulse effective repetition times (12.3, 14.8, 24.8, 39.8, 59.8, and 99.2 ms, respectively, n=3). The curve shown was fitted using an exponential curve (R-squared values>0.88). Panel B, similarly contains a graph plotting the adenosine (ADO) peak current of an S voltammogram at 1.45V potential. Panel C, similarly contains a graph plotting the ΔpH peak current of an S voltammogram at −0.1V potential.

In order to further investigate the effect of PPV repetition time, PPV data were obtained using six different gap times (2.5, 5, 15, 30, 50, and 90 ms), which respectively corresponded to the secondary pulse effective repetition times (12.3, 14.8, 24.8, 39.8, 59.8, and 99.2 ms), at a 5 Hz PPV repetition time. Three measurements for each gap time were conducted for dopamine (1 µM), adenosine (5 µM), and ΔpH 0.1. The average and standard deviation of the three oxidation current measurements were plotted against gap time for each DA, ADO, and pH secondary voltammograms (FIG. 4). The current in the S voltammogram at 0.6V potential for DA was 9.8 nA with 12.3 ms of effective repetition time, reaching a plateau of approximately 17.0 nA with an effective repetition time of 59.8 ms. DA initially adsorbed at high rate, and then slowed, nearing saturation as the time gap between the two pulses comprising the binary waveform increased (FIG. 4; panel A). The curve fit well with the following exponential equation (R-squared values>0.88):

$$f(t) = a\left[1 - \exp\left(-\frac{t}{b}\right)\right] \quad (2)$$

where t is the effective repetition time, and a and b are fitting coefficients such that 'a' is the saturated current value when repetition time would be infinite, and 'b' is the coefficient of adsorption time, or the time required to reach approximately 63% of the saturated current value.

The DA current response with respect to PPV repetition time fit with the above exponential function with a 0.94 R-squared value. For ADO, the current versus repetition time curve fit with equation (2) with an R-square value of 0.88. The adsorption time constant 'b' for DA at 0.6V was about 14.9 ms, whereas the adsorption time constant of ADO at 1.49V potential was 35.9 ms, approximately two times slower than DA (FIG. 4; panel B). Comparatively, adsorption response for pH change was the fastest, measuring at approximately 6.5 ms. The fast H+ ion adsorption to the CFM surface resulted in near complete removal of pH change visible in the difference (P-S) voltammogram (FIG. 4; panel C).

The adsorption time coefficient described herein, is useful for characterizing each analyte and aiding in distinguishing molecules from one another in otherwise complicated or ambiguous conventional FSCV datasets. The adsorption time can be influenced by the analyte's molecular size, mass, charge, and other characteristics, which can be investigated to understand the complex dynamics of microelectrode species detection.

Evaluation of PPV in Mixtures

Figure 5:
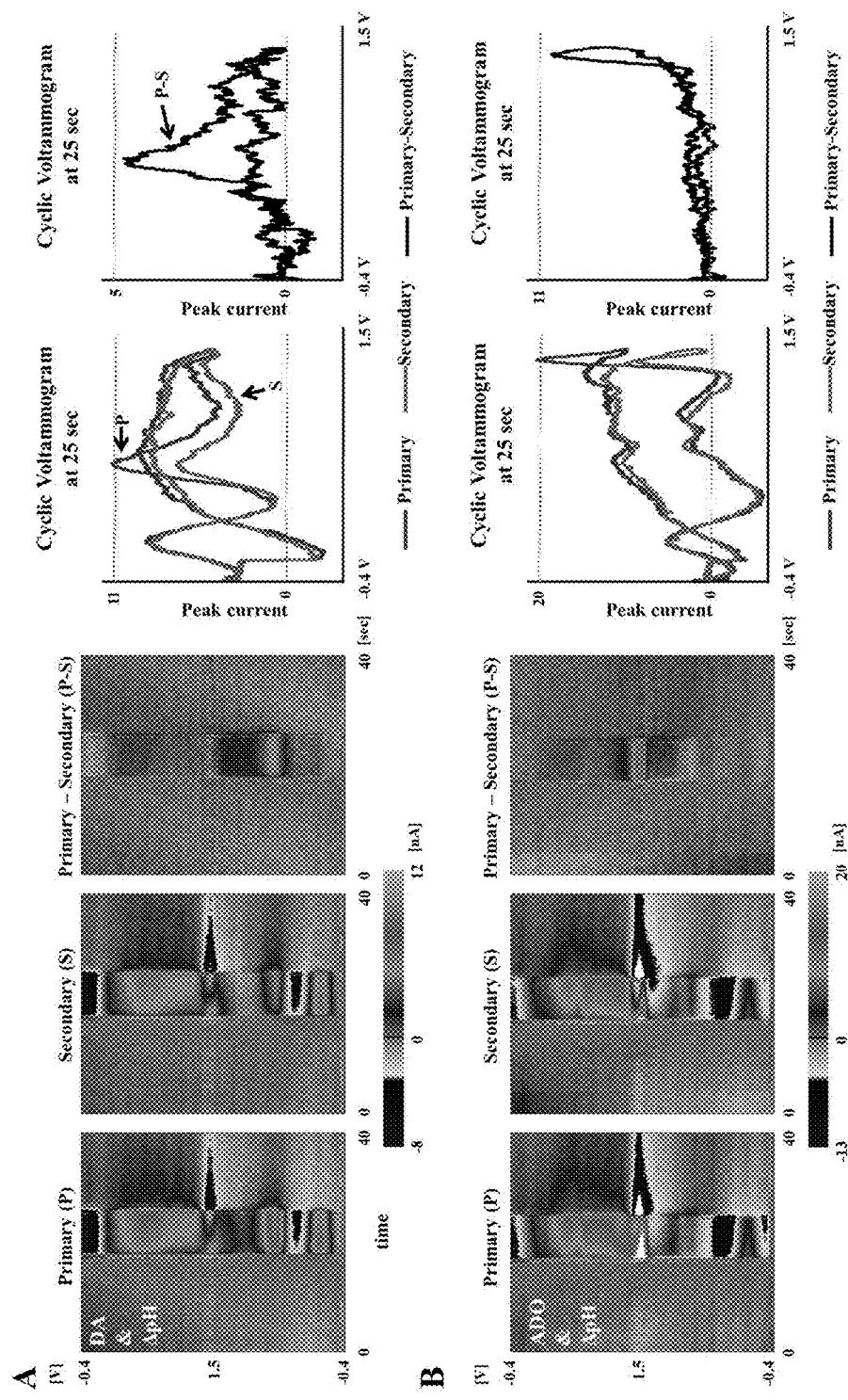
FIG. 5 contains data of PPV responses in mixtures. PPV was evaluated for resolving mixture solutions of 1 μM DA with 0.1 ΔpH (Panel A) and 5 μM ADO with 0.1 ΔpH (Panel B). Panel A shows PPV with a 2.5 ms gap in a DA 1 μM and 0.1 ΔpH mixture solution. The P-S voltammogram revealed the DA oxidation peak as significant, with minimized ΔpH influence. Panel B shows PPV with a 2.5 ms gap in an ADO 5 μM and 0.1 ΔpH mixture solution. The reduced influence of ΔpH was more evident in the mixture containing ADO than the mixture containing DA.

To further test its capability, PPV was evaluated for resolving mixture solutions of 1 µM DA with 0.1 ΔpH and 5 µM ADO with 0.1 ΔpH. The combination of ΔpH and DA produced visually complicated P and S voltammograms in which it was difficult to differentiate individual components (FIG. 5; panel A). However, the P-S voltammogram revealed the DA oxidation peak as significant, with minimized ΔpH influence. The reduced influence of ΔpH was more evident in the mixture solution with ADO than with DA, because the adsorption time coefficient 'b' of ADO is greater than that of DA (FIG. 5; panel B). Although pH change was nearly completely removed, only the first oxidation peak of ADO was detected in the P-S voltammogram. The second oxidation peak appeared independent of the effective repetition time and had similar intensity in the primary and secondary voltammograms, therefore cancelling out in the P-S voltammogram.

Another finding was that the P-S voltammogram appeared stable around the switching potential; whereas conventional FSCV can often exhibit noticeable current changes (FIG. 5). There were no detectable current changes due to background drift or electrode surface environmental changes. Since these changes related to electrode conditioning were unlikely to depend on the repetition time, they reflected equally on the P and S voltammetry, only to cancel out and result in very reliable P-S voltammetry.

The properties of P-S voltammetry can be used in evaluating in vivo recordings, especially in human electro-chemistry where the data sets often get complex by numerous changes occurring at the microelectrode surface.

Evaluation of PPV In Vivo

Figure 6:
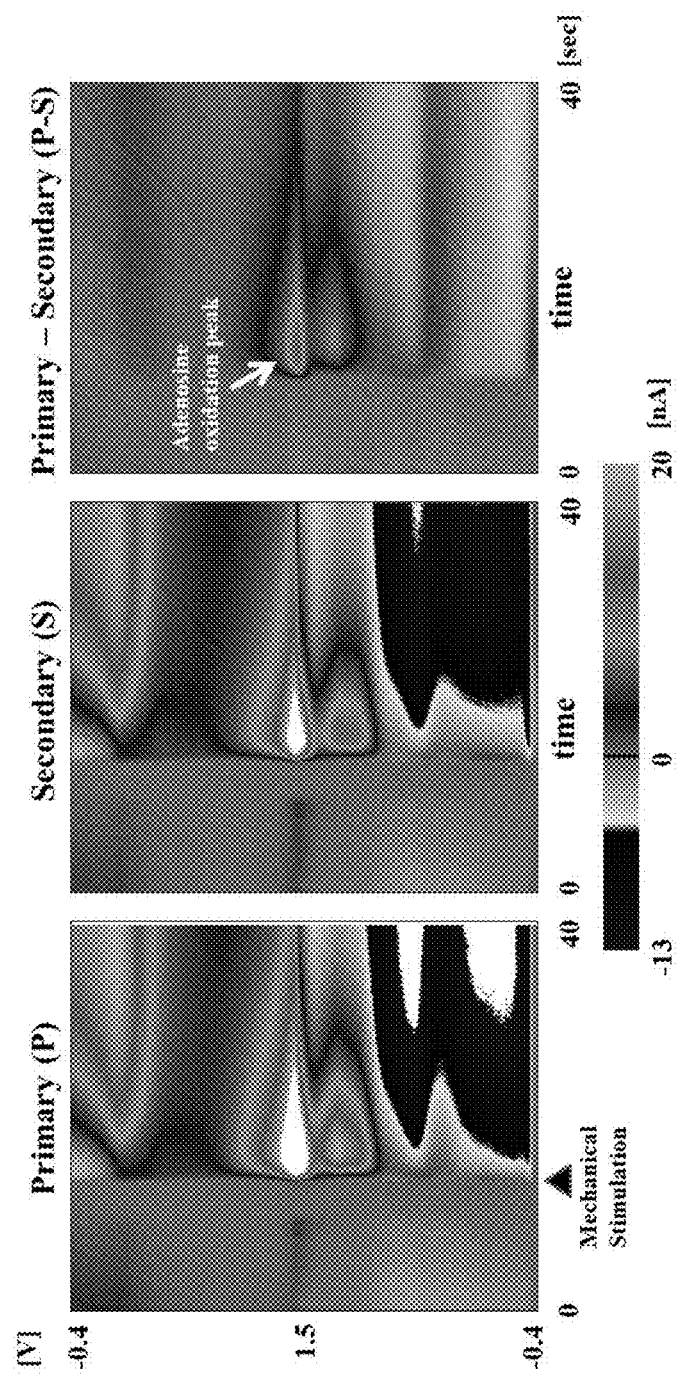
FIG. 6 contains three graphs of an evaluation of PPV in an in vivo experiment. After insertion of the cerebral function monitoring (CFM) electrode in the thalamus of a rat brain, the surface was lightly touched in order to evoke an ADO release while recording. By applying PPV with a 2.5 ms gap, only ADO responses were realized, while minimizing the effect of electrode environmental condition changes on the P-S voltammetry.

To evaluate the performance of PPV in vivo, PPV was applied in rat brain experiments for ADO detection. There are large pools of adenosine stored in the astrocytes that can be released by mechanical stimulation (Tawfik et al., *Neurosurgery*, 67:367-75 (2010); Halassa et al., *Neuron*, 61:213-219 (2009)). In order to release adenosine, mechanical stimulation of the rat brain was used. After insertion of the CFM electrode in the thalamus, the surface was lightly touched in order to evoke ADO release while recording. CFM touching induced current changes from ADO release as well as variations due to micro-environmental electrode condition changes (FIG. 6). By applying PPV with a 2.5 ms gap time, only ADO responses were realized, while minimizing the effect of electrode environmental condition changes on the P-S voltammetry. An interesting finding was the clear second oxidation peak at 1.2V in the P-S voltammogram, which was not observed in the in vitro ADO detection experiments (FIG. 3; panel B). This might be due to a different micro-environment around the electrode during the in vivo experiments, altering the analyte adsorption at CFM surface when compared to in vitro experiments. It could also be a response to the other metabolites being released in the brain during mechanical stimulation.

In conventional FSCV, the time-varying potential is a brief pyramidal waveform, typically repeated 10 times per second. The CFM is otherwise maintained at a specified holding potential with respect to the reference electrode. As described herein, PPV was used where the waveforms are paired in doublets—two identical waveforms ("pulses"), separated in time by an arbitrary but short interval at the holding potential. The results provided herein demonstrate that PPV can discriminate analytes based on their adsorption characteristics. When the voltammogram for one of the pulses comprising a doublet is subtracted from the voltammogram for the other pulse, the effects of pH change, for example, were largely eliminated.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A system for assessing a characteristic of an analyte in an environment, the system comprising:
   a set of electrodes, including a working electrode and a reference electrode;
   a controller configured to vary an electrical potential applied between the working electrode and the reference electrode according to a binary waveform while the set of electrodes are located in the environment, wherein the binary waveform includes:
      (i) a primary pulse that spans a first time interval, and
      (ii) a secondary pulse that spans a second time interval following the first time interval;
   a data acquisition apparatus configured to record:
      (i) a primary data set that includes a first plurality of samples acquired over the first time interval, each sample indicating a respective level of electrical current measured at the working electrode at a corresponding time at which the sample was acquired, and
      (ii) a secondary data set that includes a second plurality of samples acquired over the second time interval, each sample indicating a respective level of electrical current measured at the working electrode at a corresponding time at which the sample was acquired;
   a computing system, including one or more processors, configured to perform operations comprising:
      generating, using the primary data set, a first voltammogram that characterizes a response to the primary pulse at the working electrode over the first time interval;
      generating, using the secondary data set, a second voltammogram that characterizes a response to the secondary pulse at the working electrode over the second time interval;
      generating a difference voltammogram by determining a respective difference between the first voltammogram and the second voltammogram at corresponding times between the first time interval and the second time interval; and
      determining the characteristic of the analyte in the environment using the difference voltammogram.

2. The system of claim 1, wherein the controller is further configured to repeatedly vary the electrical potential applied between the working electrode and the reference electrode according to the binary waveform while the set of electrodes are located in the environment at a frequency defined by a repetition time interval.

3. The system of claim 2, wherein the controller holds the electrical potential applied between the working electrode and the reference electrode at a base level from the end of the secondary pulse of a first binary waveform to the start of the primary pulse of a second binary waveform that immediately follows the first binary waveform.

4. The system of claim 2, wherein the repetition time interval is selected from a range of about 30 milliseconds to about 1000 milliseconds.

5. The system of claim 2, wherein the primary pulses of each of a series of successive binary waveforms that the controller applies as electrical potentials between the working electrode and the reference electrode are identical, wherein the secondary pulses of each of the series of successive binary waveforms are identical.

6. The system of claim 1, wherein the binary waveform further includes a gap time interval between the first time interval and the second time interval during which the electrical potential applied between the working electrode and the reference electrode is held at a baseline level to separate the primary pulse from the secondary pulse.

7. The system of claim 6, wherein:
   a primary pulse effective repetition time interval identifies a time lapse between the start of the secondary pulse of a first binary waveform and the start of the primary pulse of a second binary waveform that immediately follows the first binary waveform; and
   the primary pulse effective repetition time interval is greater than the gap time interval.

8. The system of claim 6, wherein the gap time interval is selected from a range of about 1 millisecond to about 100 milliseconds.

9. The system of claim 1, wherein the primary pulse is shaped such that the electrical potential applied between the working electrode and the reference electrode during the primary pulse ascends from a baseline level to a peak level and then descends from the peak level to the baseline level.

10. The system of claim 9, wherein the baseline level of the electrical potential applied between the working electrode and the reference electrode is −0.4 Volts, wherein the peak level of the electrical potential applied between the working electrode and the reference electrode is 1.5 Volts.

11. The system of claim 9, wherein the primary pulse is a triangle waveform that (i) ramps up at a constant rate from the baseline level of electrical potential to the peak level of electrical potential and (ii) ramps down at a constant rate from the peak level of electrical potential to the baseline level of electrical potential.

12. The system of claim 1, wherein the primary pulse of the binary waveform is identical to the secondary pulse of the binary waveform.

13. The system of claim 1, wherein the environment is a brain of a mammal, wherein the analyte is dopamine or adenosine.

14. The system of claim 1, wherein determining the characteristic of the analyte in the environment comprises determining a concentration of the analyte in the environment.

15. A method, comprising:
   applying an electrical potential between a working electrode and a reference electrode that are located in a solution that contains an analyte;
   varying the electrical potential between the working electrode and the reference electrode according to a binary waveform that includes:
      (i) a primary pulse that spans a first time interval, and
      (ii) a secondary pulse that spans a second time interval following the first time interval;
   obtaining a primary data set and a secondary data set, wherein:
      (i) the primary data set includes a first plurality of samples acquired over the first time interval, each sample indicating a respective level of electrical current measured at the working electrode at a corresponding time at which the sample was acquired, and
      (ii) the secondary data set includes a second plurality of samples acquired over the second time interval, each sample indicating a respective level of electrical current measured at the working electrode at a corresponding time at which the sample was acquired;
   generating, by a computing system and using the primary data set, a first voltammogram that characterizes a response to the primary pulse at the working electrode over the first time interval;

generating, by the computing system and using the secondary data set, a second voltammogram that characterizes a response to the secondary pulse at the working electrode over the second time interval;

generating a difference voltammogram by determining a respective difference between the first voltammogram and the second voltammogram at corresponding times between the first time interval and the second time interval; and determining the characteristic of the analyte in the environment using the difference voltammogram.

16. The method of claim 15, wherein the binary waveform further includes a gap time interval between the first time interval and the second time interval during which the electrical potential applied between the working electrode and the reference electrode is held at a baseline level to separate the primary pulse from the secondary pulse.

17. The method of claim 16, wherein the gap time interval is selected from a range of about 1 millisecond to about 100 milliseconds.

18. The method of claim 15, wherein the primary pulse is shaped such that the electrical potential applied between the working electrode and the reference electrode during the primary pulse ascends from a baseline level to a peak level and then descends from the peak level to the baseline level.

19. The method of claim 18, wherein the baseline level of the electrical potential applied between the working electrode and the reference electrode is −0.4 Volts, wherein the peak level of the electrical potential applied between the working electrode and the reference electrode is 1.5 Volts.

20. The method of claim 18, wherein the primary pulse is a triangle waveform that (i) ramps up at a constant rate from the baseline level of electrical potential to the peak level of electrical potential and (ii) ramps down at a constant rate from the peak level of electrical potential to the baseline level of electrical potential.

21. The method of claim 15, wherein the primary pulse of the binary waveform is identical to the secondary pulse of the binary waveform.

* * * * *